(12) United States Patent
Erez

(10) Patent No.: US 10,977,388 B2
(45) Date of Patent: *Apr. 13, 2021

(54) COMPUTER SYSTEM OF COMPUTER SERVERS AND DEDICATED COMPUTER CLIENTS SPECIALLY PROGRAMMED TO GENERATE SYNTHETIC NON-REVERSIBLE ELECTRONIC DATA RECORDS BASED ON REAL-TIME ELECTRONIC QUERYING AND METHODS OF USE THEREOF

(71) Applicant: MDClone Ltd., Beer-Sheva (IL)

(72) Inventor: Luz Erez, Meitar (IL)

(73) Assignee: MDCLone Ltd., Beer-Sheva (IL)

( * ) Notice: Subject to any disclaimer, the term of this patent is extended or adjusted under 35 U.S.C. 154(b) by 3 days.

This patent is subject to a terminal disclaimer.

(21) Appl. No.: 16/356,846

(22) Filed: Mar. 18, 2019

(65) Prior Publication Data

US 2019/0278943 A1 Sep. 12, 2019

Related U.S. Application Data

(63) Continuation of application No. 15/968,194, filed on May 1, 2018, now Pat. No. 10,235,537, which is a
(Continued)

(51) Int. Cl.
*G06F 16/00* (2019.01)
*G06F 21/62* (2013.01)
(Continued)

(52) U.S. Cl.
CPC ........ *G06F 21/6254* (2013.01); *G06F 3/0482* (2013.01); *G06F 3/04847* (2013.01);
(Continued)

(58) Field of Classification Search
CPC .. G06F 16/248; G06F 16/9038; G06F 21/602; G06F 21/6245; G06F 21/6254;
(Continued)

(56) References Cited

U.S. PATENT DOCUMENTS 6,574,629 B1 * 6/2003 Cooke, Jr. ............... G16H 30/20
8,577,933 B2 * 11/2013 Evenhaim ........... G06F 21/6254
707/809
(Continued)

*Primary Examiner* — Diedra McQuitery
(74) *Attorney, Agent, or Firm* — Greenberg Traurig, LLP

(57) ABSTRACT

In some embodiments, the present invention provides for an exemplary computer system which includes at least: a graphical user interface client; a dedicated application server; the dedicated application server is configured to connect to the graphical user interface client and an electronic source with electronic data records; where the electronic data records include real identification identifiers of real individuals; where the graphical user interface client is configured to generate at a graphical user interface that is configured to receive user authenticating credential information and to conduct a real-time electronic negotiation querying session between the user and the dedicated application server to generate a plurality of non-reversible synthetic electronic data records of a plurality of synthetic individuals, by utilizing at least one statistical technique so that the plurality of non-reversible synthetic electronic data records cannot be used to identify any real individual in the plurality of electronic data records.

2 Claims, 23 Drawing Sheets

Related U.S. Application Data continuation of application No. 15/592,779, filed on May 11, 2017, now Pat. No. 9,965,650.

(60) Provisional application No. 62/334,952, filed on May 11, 2016.

(51) Int. Cl.
| | | |
|---|---|---|
| *G06F 3/0484* | (2013.01) | |
| *G06F 3/0482* | (2013.01) | |
| *G16H 10/60* | (2018.01) | |
| *G06F 16/9038* | (2019.01) | |
| *G06F 16/248* | (2019.01) | |
| *G06F 21/60* | (2013.01) | |
| *H04L 9/06* | (2006.01) | |

(52) U.S. Cl.
CPC ........ *G06F 16/248* (2019.01); *G06F 16/9038* (2019.01); *G06F 21/6245* (2013.01); *G16H 10/60* (2018.01); *G06F 21/602* (2013.01); *H04L 9/0618* (2013.01); *H04L 2209/42* (2013.01)

(58) Field of Classification Search
CPC ... G06F 3/0482; G06F 3/04847; G16H 10/60; H04L 2209/42; H04L 9/0618
See application file for complete search history.

(56) References Cited

U.S. PATENT DOCUMENTS

| | | | | |
|---|---|---|---|---|
| 2010/0131573 | A1* | 5/2010 | Reese | G06F 16/16 707/812 |
| 2015/0073830 | A1* | 3/2015 | Hill | G06Q 30/0204 705/3 |
| 2015/0288665 | A1* | 10/2015 | El Emam | H04L 9/008 713/171 |

* cited by examiner

MDClone Synthetic Data Automatic Report (Draft)

Introduction

The following is a report comparing 's original data to the Synthetic Data created by MDClone. The comparison includes the following information:

1. The number of rows of data in the original data set, and in the synthetic data set.
2. A comparison of the distribution of each variable in the original data set versus MDClone Synthetic data.
3. A comparison of the correlation of all pairs of variables, Original data versus MDClone Synthetic data.

The distribution of each variable will be displayed in a way which enables easy visual comparison of the similarity between the original data's distribution to the synthetic one. If the plot on the left looks like the plot on its right - the distribution is similar. If they look different, then there is a problem. Using a mild technical jargon, we present for each variable a "violin plot" which is a box plot with a rotated kernel density plot on each side. This enables the reader to see a much better picture of variables characteristics (compared, for example to a summary of the minimum, median and maximum values, or to a summary containing the average and variance of the variable). For example, the following figure is a violin plot for a sample of size 10,000 from a standard Normal distribution:

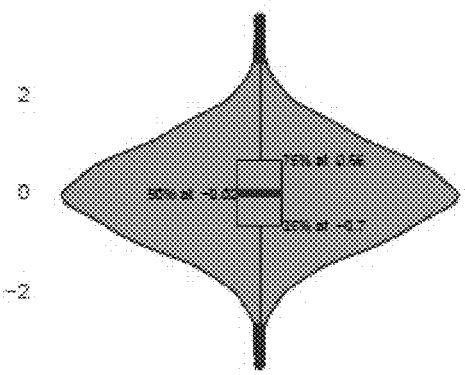

*Fig. 7A*

As can be seen, the figure has a shape of the density plot of a normal distribution, mirrored to both sizes. The next figure is a violin plot for a similar size sample, from a Uniform distribution.

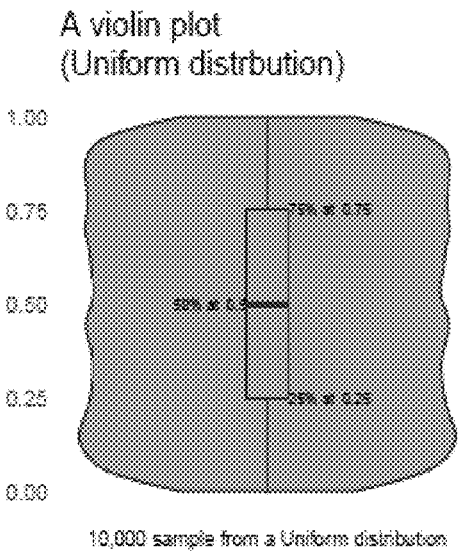

10,000 sample from a Uniform distribution

We'll use such violin plots to compare the distribution of the Original data variables to the distribution of their MDClone Synthetic data counterparts. For illustration, the next figure is such a comparison for a variable which resembles a Beta distribution and its Synthetic output:

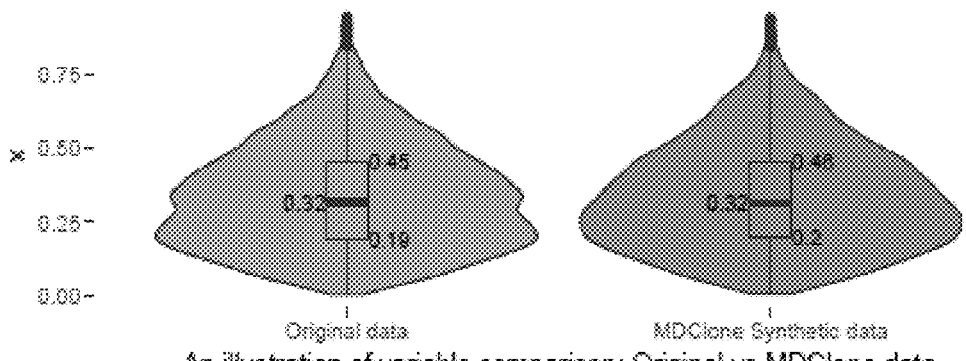

An illustration of variable comparison: Original vs MDClone data

It is easily seen that while the distribution of the original variable (on the left side) is not identical to MDClone's Synthetic counterpart output, they are very similar to each other.
When the two plots (original vs. MDClone distribution for a specific variable) do not resemble one another, there is a problem. Here's an illustration:

COMPUTER SYSTEM OF COMPUTER SERVERS AND DEDICATED COMPUTER CLIENTS SPECIALLY PROGRAMMED TO GENERATE SYNTHETIC NON-REVERSIBLE ELECTRONIC DATA RECORDS BASED ON REAL-TIME ELECTRONIC QUERYING AND METHODS OF USE THEREOF

RELATED APPLICATIONS

This application is a continuation of U.S. patent application Ser. No. 15/968,194, filed May 1, 2018, which is a continuation of U.S. patent application Ser. No. 15/592,779, filed May 11, 2017, which claims priority of U.S. Provisional Appln. No. 62/334,952, filed May 11, 2016, which are incorporated herein by reference in their entirety for all purposes.

FIELD OF TECHNOLOGY

The subject matter herein generally relates to computer system of computer servers and dedicated computer clients specially programmed to generate synthetic non-reversible electronic data records based on real-time electronic negotiation querying and methods of use thereof.

BACKGROUND OF THE INVENTION

For example, a typical electronic quirying can involve an electronic exchange one or more eletronic messages having software-based query construction(s) of one or more variable-value pairs between a particular software client and its dedicated server, where the software client resides remotely form its dedicated server.

SUMMARY OF THE INVENTION

In some embodiments, the present invention provides for an exemplary computer system which includes at least the following components: at least one graphical user interface client; at least one dedicated application server; where the at least one dedicated application server at least includes: a non-transitory memory storing instructions and at least one server processor; where, when executing the instructions by the at least one server processor, the at least one dedicated application server is configured to operationally connect to the at least one graphical user interface client and at least one electronic source with a plurality of electronic data records; where the plurality of electronic data records includes at least 10,000 data records; where the plurality of electronic data records includes real identification identifiers of real individuals; where the at least one graphical user interface client is configured to utilize at least one processor of a computing device of a user to: generate at least first graphical user interface that includes: i) at least one first programmable software object which is configured to receive user authenticating credential information; where the at least one dedicated application server is configured to assign an anonymity level to the user based on user authenticating credential information; ii) a plurality of second programmable software objects which are configured to conduct at least one real-time electronic negotiation querying session between the user and the at least one dedicated application server; where the at least one real-time electronic negotiation querying session is configured to: 1) receive, from the user, via the plurality of second programmable software objects, at least the following: a) at least one of: a plurality of personal event data parameters of at least one personal event and at least one demographic identifier, and b) a plurality of reference event data parameters of at least one reference event, where the plurality of reference event data parameters of the at least one reference event include a plurality time-related property data parameters for at least one time-related property of the at least one reference event; 2) allow, the user, via the plurality of second programmable software objects, to iteratively adjust the plurality of personal event data parameters of the at least one personal event and at least one of the at least one demographic identifier and the plurality of reference event data parameters of the at least one reference event so that, based on the anonymity level of the user, there is a matched subset of a minimal number of real individuals associated with the plurality of electronic data records of the at least one electronic source match the at least one personal event and the at least one reference event; 3) display, in real-time, an indication of how many real individuals are in the matched subset; 4) generate, with each adjustment iteration, a plurality of non-reversible synthetic electronic data records of a plurality of synthetic individuals, by utilizing at least one statistical technique to perform at least one of: self-recalculation of discrete values of the plurality of electronic data records of the matched subset and self-transformation categorical values of the plurality of electronic data records of the matched subset; and 5) electronically output, for the user, the plurality of non-reversible synthetic electronic data records of the plurality of synthetic individuals to at least one electronic destination associated with the user; and where the plurality of non-reversible synthetic electronic data records of the plurality of synthetic individuals: a) are statistically representative of the matched subset, b) have at least one synthetic identification identifier corresponding to at least one real identification identifier of a real individual from the matched subset, and c) cannot be utilized to identify any real individual from the matched subset.

In some embodiments, the at least one dedicated application server is configured to assign the anonymity level to the user based on an entity affiliation of the user.

In some embodiments, the at least one statistical technique is a conditional probability methodology.

In some embodiments, the at least one real-time electronic negotiation querying session is further configured to generate at least one comparison report, analyzing all pairs of variables between the plurality of electronic data records of the matched subset and the plurality of non-reversible synthetic electronic data records of the plurality of synthetic individuals.

In some embodiments, the at least one comparison report is generated based on pearson's correlation for each pairs of variables between the plurality of electronic data records of the matched subset and the plurality of non-reversible synthetic electronic data records of the plurality of synthetic individuals.

In some embodiments, the plurality of electronic data records are a plurality of electronic medical records.

In some embodiments, the plurality of non-reversible synthetic electronic data records of the plurality of synthetic individuals are HIPAA self-compliant.

In some embodiments, the at least one synthetic identification identifier is de-identification identifier which is required, based on HIPAA, to be removed from the plurality of electronic data records of the matched subset prior to being outputted to the at least one electronic destination associated with the user.

In some embodiments, the present invention provides for an exemplary computer system which includes at least the following steps: causing to install at least one graphical user interface client on a computing device of a user; where the at least one graphical user interface client is configured to operationally connect to at least one dedicated application server; where the at least one dedicated application server includes: a non-transitory memory storing instructions and at least one server processor; where, when executing the instructions by the at least one server processor, the at least one dedicated application server is configured to operationally connect to the at least one graphical user interface client and at least one electronic source with a plurality of electronic data records; where the plurality of electronic data records includes at least 10,000 data records; where the plurality of electronic data records includes real identification identifiers of real individuals; where the at least one graphical user interface client is configured to utilize at least one processor of the computing device of the user to: generate at least first graphical user interface that includes: i) at least one first programmable software object which is configured to receive user authenticating credential information; where the at least one dedicated application server is configured to assign an anonymity level to the user based on user authenticating credential information; ii) a plurality of second programmable software objects which are configured to conduct at least one real-time electronic negotiation querying session between the user and the at least one dedicated application server; where the at least one real-time electronic negotiation querying session is configured to: 1) receive, from the user, via the plurality of second programmable software objects, at least the following: a) at least one of: a plurality of personal event data parameters of at least one personal event and at least one demographic identifier, and b) a plurality of reference event data parameters of at least one reference event, where the plurality of reference event data parameters of the at least one reference event include a plurality time-related property data parameters for at least one time-related property of the at least one reference event; 2) allow, the user, via the plurality of second programmable software objects, to iteratively adjust the plurality of personal event data parameters of the at least one personal event and at least one of the at least one demographic identifier and the plurality of reference event data parameters of the at least one reference event so that, based on the anonymity level of the user, there is a matched subset of a minimal number of real individuals associated with the plurality of electronic data records of the at least one electronic source match the at least one personal event and the at least one reference event; 3) display, in real-time, an indication of how many real individuals are in the matched subset; 4) generate, with each adjustment iteration, a plurality of non-reversible synthetic electronic data records of a plurality of synthetic individuals, by utilizing at least one statistical technique to perform at least one of: self-recalculation of discrete values of the plurality of electronic data records of the matched subset and self-transformation categorical values of the plurality of electronic data records of the matched subset; and 5) electronically output, for the user, the plurality of non-reversible synthetic electronic data records of the plurality of synthetic individuals to at least one electronic destination associated with the user; and where the plurality of non-reversible synthetic electronic data records of the plurality of synthetic individuals: a) are statistically representative of the matched subset, b) have at least one synthetic identification identifier corresponding to at least one real identification identifier of a real individual from the matched subset, and c) cannot be utilized to identify any real individual from the matched subset.

BRIEF DESCRIPTION OF THE DRAWINGS

The present invention can be further explained with reference to the attached drawings, wherein like structures are referred to by like numerals throughout the several views. The drawings shown are not necessarily to scale, with emphasis instead generally being placed upon illustrating the principles of the present invention. Therefore, specific structural and functional details disclosed herein are not to be interpreted as limiting, but merely as a representative basis for teaching one skilled in the art to variously employ the present invention.

DETAILED DESCRIPTION OF THE INVENTION

Figure 1:
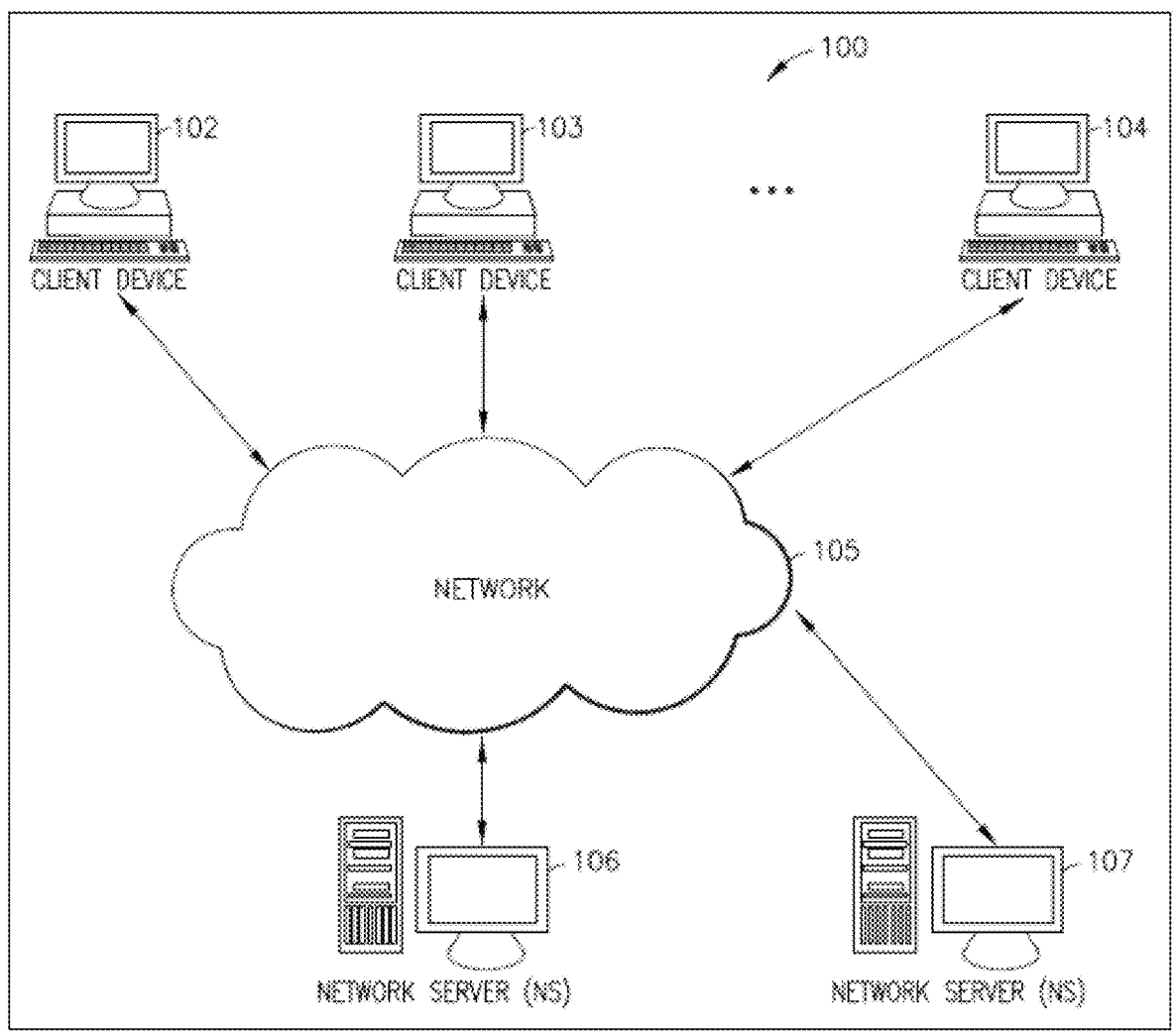
FIGS. 1-4 illustrate certain computer architectures in accordance with at least some principles of at least some embodiments of the present invention.

Among those benefits and improvements that have been disclosed, other objects and advantages of this invention can become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the present invention is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. In some embodiments, the terms "instantaneous," "instantaneously," "instantly,"

and "in real time" refer to a condition where a time difference between a first time when a search request is transmitted and a second time when a response to the request is received is no more than 1 second. In some embodiments, the time difference between the request and the response is between less than 1 second and several seconds (e.g., 5-10 seconds).

As used herein, the term "dynamic(ly)" means that events and/or actions can be triggered and/or occur without any human intervention. In some embodiments, events and/or actions in accordance with the present invention can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

In some embodiments, the inventive electronic systems are associated with electronic mobile devices (e.g., smartphones, etc.) of users and server(s) in the distributed network environment, communicating over a suitable data communication network (e.g., the Internet, etc.) and utilizing at least one suitable data communication protocol (e.g., IPX/SPX, X.25, AX.25, AppleTalk™, TCP/IP (e.g., HTTP), etc.). In some embodiments, a plurality of concurrent users can be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-10,000,000,000).

Illustrative Exemplary Operating Environments

FIG. 1 illustrates one embodiment of an environment in which the exemplary specially programmed inventive computing system of the present invention may operate. However, not all of these components may be required to practice the invention, and variations in the arrangement and type of the components may be made without departing from the spirit or scope of the invention. In some embodiments, the exemplary specially programmed inventive computing system may manage a large number of members and/or concurrent real-time negotiations (e.g., at least 10; at least 100; at least 1,000; at least, 10,000; at least 1,000,000; etc.). In other embodiments, the inventive system and method are based on a scalable computer and network architecture that incorporates various strategies for assessing the data, caching, searching, and database connection pooling. An example of the scalable architecture is an architecture that is capable of operating multiple servers.

In embodiments, users (e.g., requestors of electronic data records (EDRs)) of the exemplary specially programmed inventive computing system of the present invention can utilize virtually any computing device 102-104 (e.g., desktop computer, laptop, smartphone) which is specifically programmed to receive and send messages over a network, such as network 105, to and from servers 106 and 107 which are programmed to conduct the real-time negotiations and generate the inventive synthetic non-reversible data records (SNR EDRs). In embodiments, the set of such devices includes devices that typically connect using a wired communications medium such as personal computers, multiprocessor systems, microprocessor-based or programmable consumer electronics, network PCs, and the like. In some embodiments, the set of such devices also includes devices that typically connect using a wireless communications medium such as cell phones, smart phones, radio frequency (RF) devices, infrared (IR) devices, VR (virtual reality device), integrated devices combining one or more of the preceding devices, or virtually any mobile device, and the like. Similarly, in some embodiments, each of client devices 102-104 is any device that is capable of connecting using a wired or wireless communication medium such as a PDA, wearable computer, and any other device that is equipped to communicate over a wired and/or wireless communication medium.

In embodiments, each user device of the devices 102-104 may include the app and/or a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In embodiments, programming may include either Java, .Net, QT, C, C++ or other suitable programming language.

In embodiments, users' devices 102-104 may be further configured to receive a message from another computing device employing another mechanism, including, but not limited to email, Short Message Service (SMS), Multimedia Message Service (MMS), instant messaging (IM), internet relay chat (IRC), mIRC, Jabber, and the like or a proprietary protocol.

In embodiments, the network 105 may be configured to couple one computing device to another computing device to enable them to communicate. In some embodiments, the network 105 may be enabled to employ any form of computer readable media for communicating information from one electronic device to another. Also, in some embodiments, the network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In some embodiments, on an interconnected set of LANs, including those based on differing architectures and protocols, a router may act as a link between LANs, enabling messages to be sent from one to another.

Figure 2:
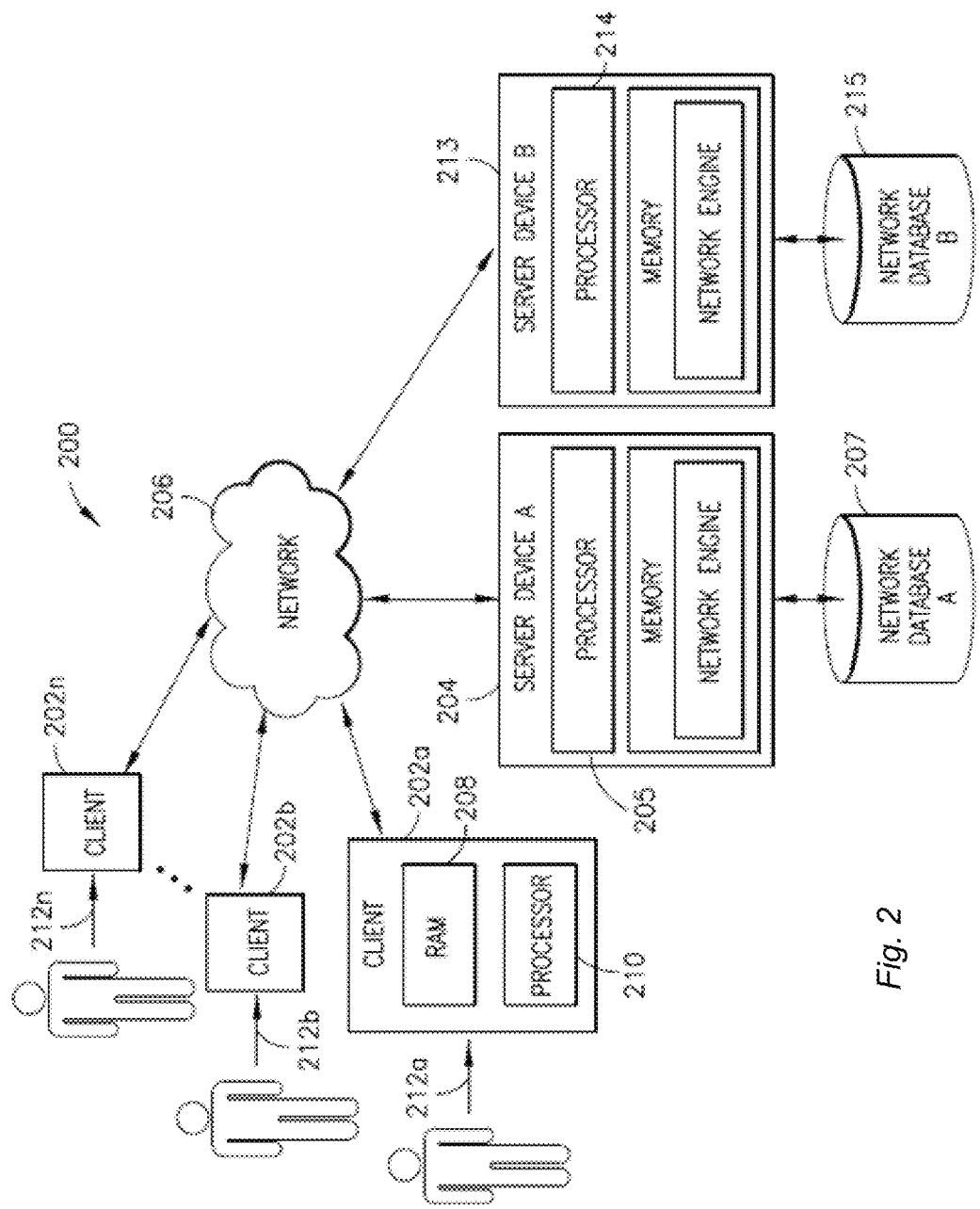

FIG. 2 shows another exemplary embodiment of the computer and network architecture that can support the exemplary inventive specifically programmed computing devices, the exemplary inventive computer-programmed systems, and the exemplary inventive computer-processing methods of the present invention. In some embodiments, each of the user devices 202a, 202b thru 202n of users (requestors of EDRs 212a, 212b, and 212n) at least includes a computer-readable medium, such as a random access memory (RAM) 208 coupled to a processor 210 or FLASH memory. In some embodiments, the processor 210 may execute computer-executable program instructions stored in memory 208. In some embodiments, such processors comprise a microprocessor, an ASIC, and state machines. In some embodiments, such processors comprise, or may be in communication with, media, for example computer-readable media, which stores instructions that, when executed by the processor, cause the processor to perform the steps described herein.

In some embodiments, types of computer-readable media may include, but are not limited to, an electronic, optical, magnetic, or other storage or transmission device capable of providing a processor, such as the processor 210 of client 202*a*, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, Ruby on Rail and JavaScript.

Figure 5:
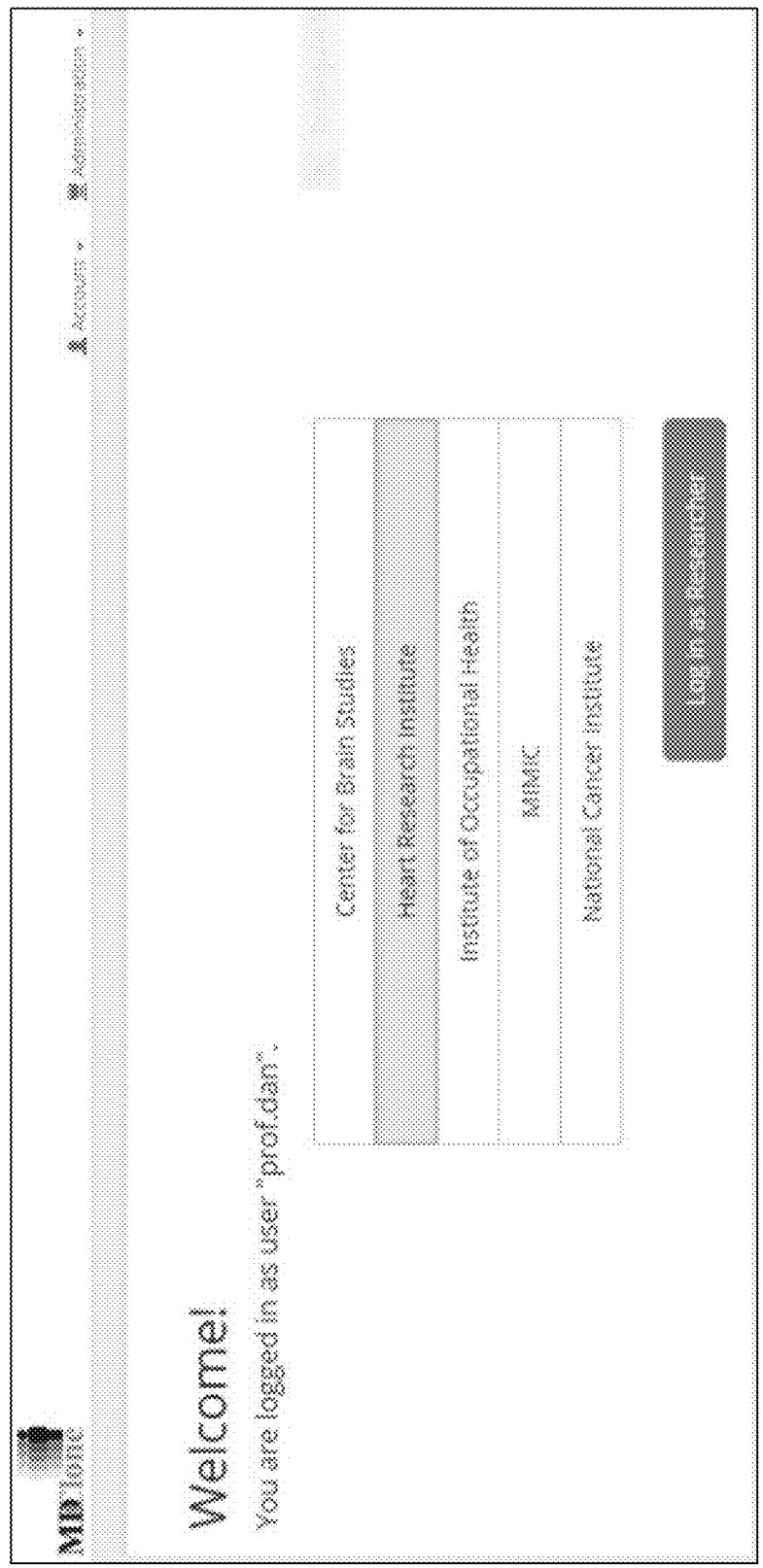
FIGS. 5-6I and 6K-6M show screenshots of computer interfaces which are representative of some exemplary aspects of the present invention in accordance with at least some principles of at least some embodiments of the present invention.

In some embodiments, member devices 202*a*-*n* may also comprise a number of external or internal devices such as a mouse, a CD-ROM, DVD, a keyboard, a display, or other input or output devices. Examples of client devices 202*a*-*n* may be personal computers, digital assistants, personal digital assistants, cellular phones, mobile phones, smart phones, pagers, digital tablets, laptop computers, Internet appliances, and other processor-based devices. In general, a client device 202*a* may be any type of processor-based platform that is connected to a network 206 and that interacts with one or more application programs. Client devices 202*a*-*n* may operate on any operating system capable of supporting a browser or browser-enabled application, such as Microsoft™, Windows™, or Linux. In some embodiments, the client devices 202*a*-*n* shown may include, for example, personal computers executing a browser application program such as Microsoft Corporation's Internet Explorer™, Apple Computer, Inc.'s Safari™, Mozilla Firefox, and Opera. Through the client devices 202*a*-*n*, users (requestors of EMRs) 212*a*-*n* communicate over the network 206 with each other and with other systems and devices coupled to the network 206. As shown in FIG. 5, server devices 204 and 213 may be also coupled to the network 206. In an embodiment of the present invention, one or more clients can be a mobile client.

In some embodiments, the term "mobile electronic device" may refer to any portable electronic device that may or may not be enabled with location tracking functionality. For example, a mobile electronic device can include, but is not limited to, personal digital assistant (PDA), Blackberry™, pager, smartphone, or any other reasonable mobile electronic device. For ease, at times the above variations are not listed or are only partially listed, this is in no way meant to be a limitation.

Figure 3:
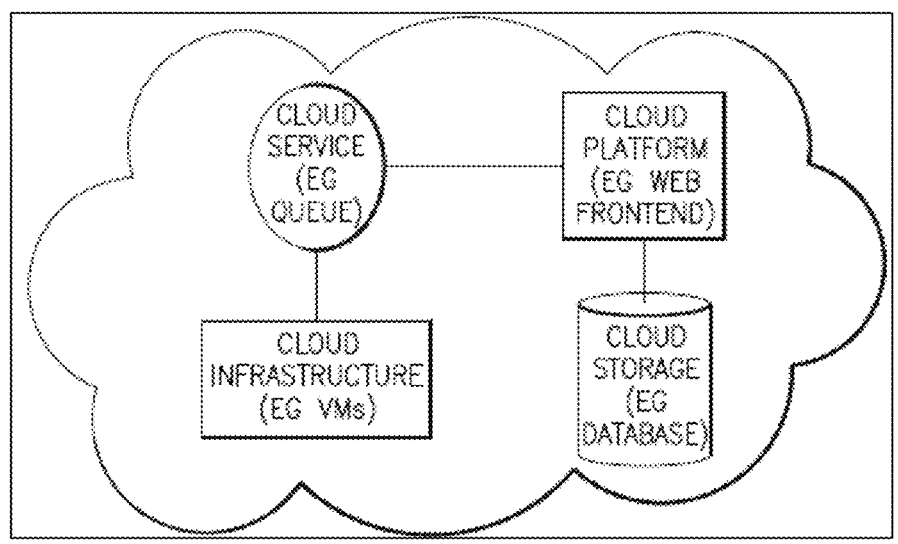
Figure 4:
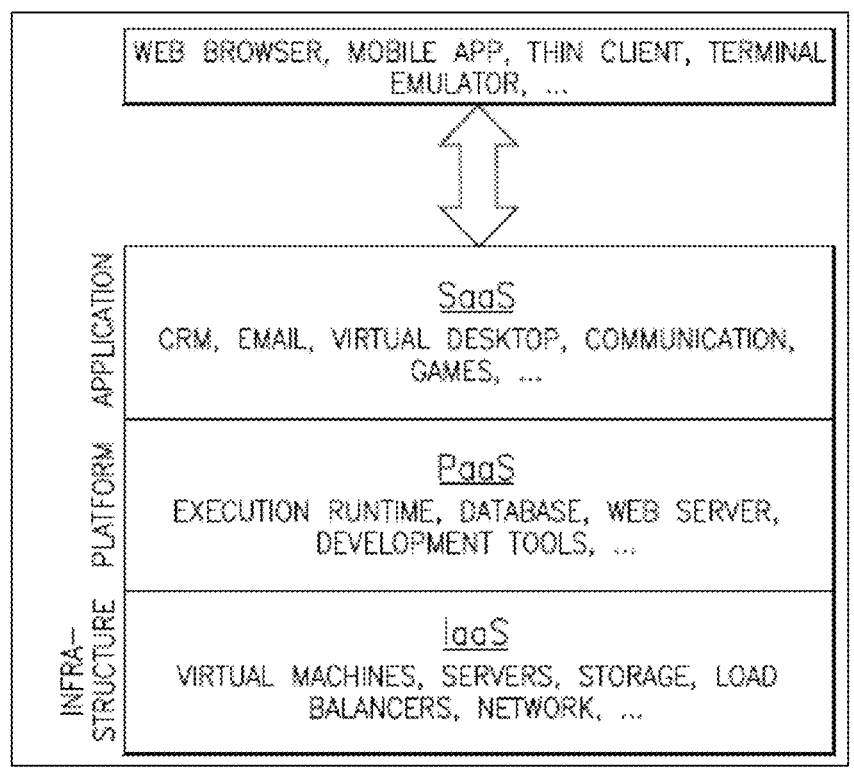

For purposes of the instant description, the terms "cloud," "Internet cloud," "cloud computing," "cloud architecture," and similar terms correspond to at least one of the following utilized by the exemplary inventive computer-programmed systems and the exemplary inventive computer-processing methods of the present invention: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). In some embodiments, the inventive computer flexible lease basis system offers/manages the cloud computing/architecture as, but not limiting to: infrastructure a service (IaaS), platform as a service (PaaS), and software as a service (SaaS). FIGS. 3 and 4 illustrate schematics of exemplary implementations of the cloud computing/architecture.

Of note, the embodiments described herein may, of course, be implemented using any appropriate hardware and/or computing software languages. In this regard, those of ordinary skill in the art are well versed in the type of computer hardware that may be used (e.g., a mainframe, a mini-computer, a personal computer ("PC"), a network (e.g., an intranet and/or the internet)), the type of computer programming techniques that may be used (e.g., object oriented programming), and the type of computer programming languages that may be used (e.g., C++, Basic, AJAX, Javascript). The aforementioned examples are, of course, illustrative and not restrictive.

As detailed herein, typically, electronic data records on a population of real individuals may have one or personal identifying attributes (identification identifiers), such as, but not limited to, names, birthdays, ages, addresses, zip codes, social security numbers; phones, etc. For example, a cable company may track records of personal viewing preferences together personal identifying information of its subscribers (identification identifiers). In another example, an internet company may track internet activity of its users together with personal identifying information. Due to privacy, identity fraud, and/or other electronic security concerns, one technological problem has been that unrelated entities would not typically electronically transfer any electronical data what might include identification identifiers, which is. In one example, to utilize data records having identification identifiers, one would need first to anonymize such data records by removing all identification identifiers that could be used to identify a specific individual or group of individuals. However, the anonymization leads to a loss of a benefit to a society due to a generalization of the underlining data records. As detailed herein, in at least some embodiments, the present invention addresses the above technical problem, by dynamically generating synthetic data records for synthetic (non-real) individuals where the synthetic data includes synthetic identification identifiers which are statistically representative (e.g., practically identical) of the real data records of the real individuals but cannot be utilized to identify the real individuals (non-reversible data). The inventive synthetic data records of the synthetic individuals are referenced herein as non-reversible electronic data records (SNR EDRs). The inventive non-reversible synthetic data records of the synthetic individuals allows previously unavailable benefits such as, but not limited to, an ability to share personal electronic data between computer systems of unrelated entities, a precision in various personalized applications drug development, treatment development, public policy development, and others. In some embodiments, as detailed herein, the exemplary computer engines/systems of the present invention generate one or more synthetic identification identifiers based on an Anonymity Level associated with a user who desires to receive the synthetic data records of the synthetic individuals.

In some embodiments, the inventive synthetic non-reversible electronic data records (SNR EDRs) are the inventive synthetic non-reversible electronic medical records (SNR EMRs) that the inventive specially programmed computing systems may be configured to generate based on the inventive real-time electronic negotiation querying. In some embodiments, the SNR EMRs can be used in a wide variety of studies performed by research entities and/or pharmaceutical companies for various purposes such as, but not limited to, personalized drug development, clinical trial development (e.g., identifying a clinical trial population) and others.

For example, a typical source EMR data object is a collection of electronic health information about an individual or a population of individuals. A typical source EMR data object includes record(s) in digital format that is/are capable of being shared across different healthcare settings. A typical source EMR data object may include record(s) with categorical/discrete/qualitative and/or quantitative data which are representative of individual identifiable information, individual health/medical information, doctors visit information, prescriptions, service providers information (e.g., MRI provider, etc.), test results information (e.g., numerical values), and other similarly suitable information.

Illustrative Examples of Inventive Computer Interfaces Configured to Realize the Inventive Real-Time Electronic Negotiation Querying in Accordance with at Least Some Embodiments of the Present Invention FIG. 5 shows a screenshot of a computer interface (graphical user interface) that the exemplary specially programmed inventive computing system may cause to be displayed to an exemplary user (e.g., a researcher) on an exemplary electronic device utilized by the exemplary user to log in to perform the inventive real-time electronic negotiation querying. For example, FIG. 5 lists exemplary five institutions which would be considered as covered entities under the HIPAA. In some embodiments, the computer interface of FIG. 5 may be displayed to the user after the exemplary specially programmed inventive computing system authenticating credential(s) from the user, confirming the user's identity and/or entity affiliation (e.g., hospital employee, pharmaceutical company's researcher, etc).

Figure 6A:
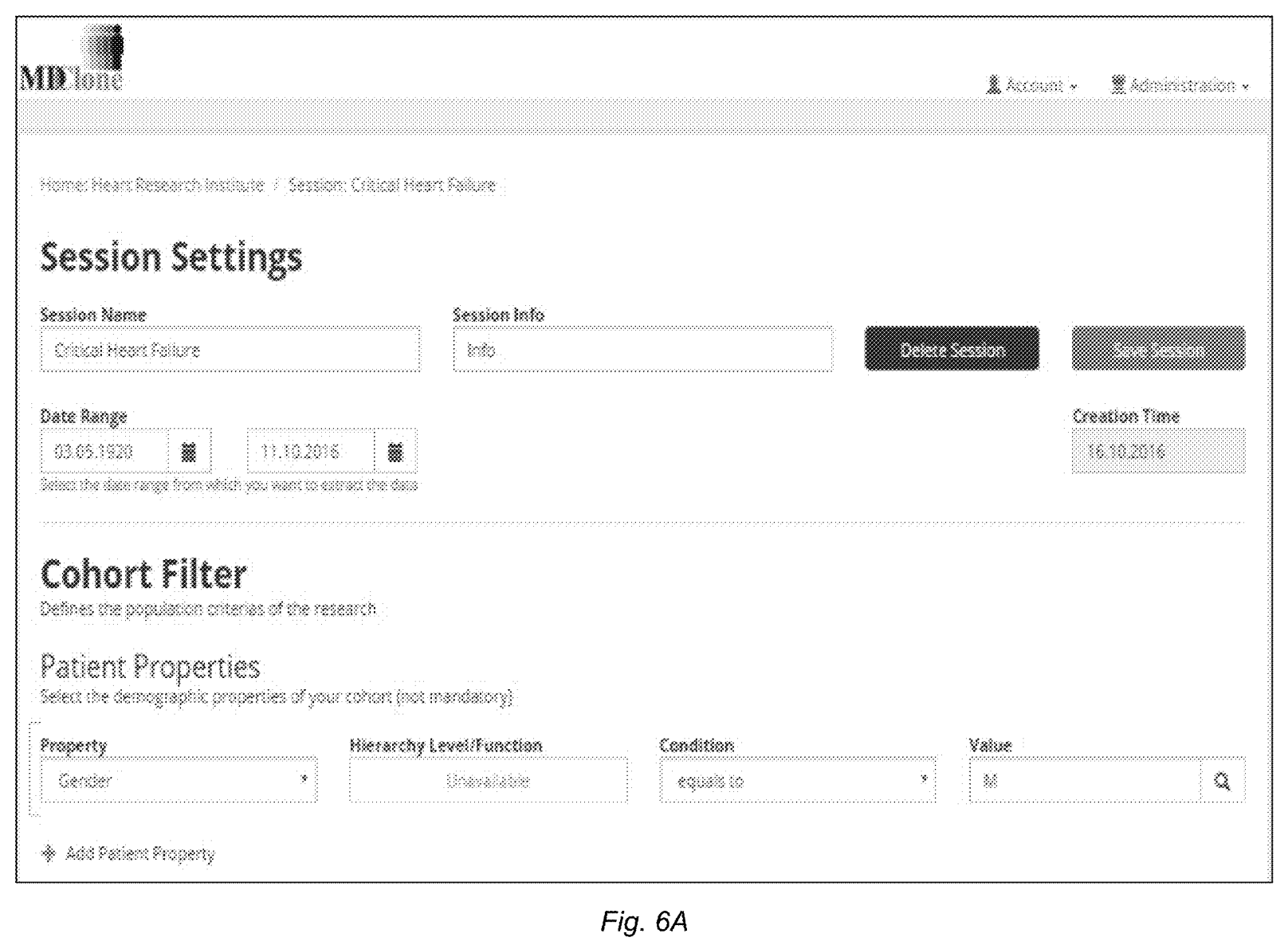

FIG. 6A shows another screenshot of another computer interface that the exemplary specially programmed inventive computing system may cause to be displayed to the exemplary user such that the user may set up parameters of an exemplary inventive real-time electronic negotiation querying session. Specifically, the user may be allowed to, for example but not limited, assign a name to the exemplary inventive real-time electronic negotiation querying session, identify a date range for a particular data sample of interest, and selecting one or more demographic properties.

FIG. 6B shows another screenshot of another computer interface that the exemplary specially programmed inventive computing system may cause to be displayed to the exemplary user such that the user may be allowed to, for example but not limited, identify one or more patient events of interest for the exemplary inventive real-time electronic negotiation querying session.

As referenced herein, the terms "personal event," "patient event," "user event," "patient event of interest," and "user event of interest" are interchangeably used and identify a particular life event of an individual. In some embodiments, the particular life event may be healthcare-related (e.g., doctor visit). In some embodiments, the particular life event may be non-healthcare-related. For example, an exemplary user event may be any one of the following, but not limited to: a medical procedure, an image (e.g., X-ray or MRI image), a drug, a prescription, a laboratory result, etc.

Figure 6C:
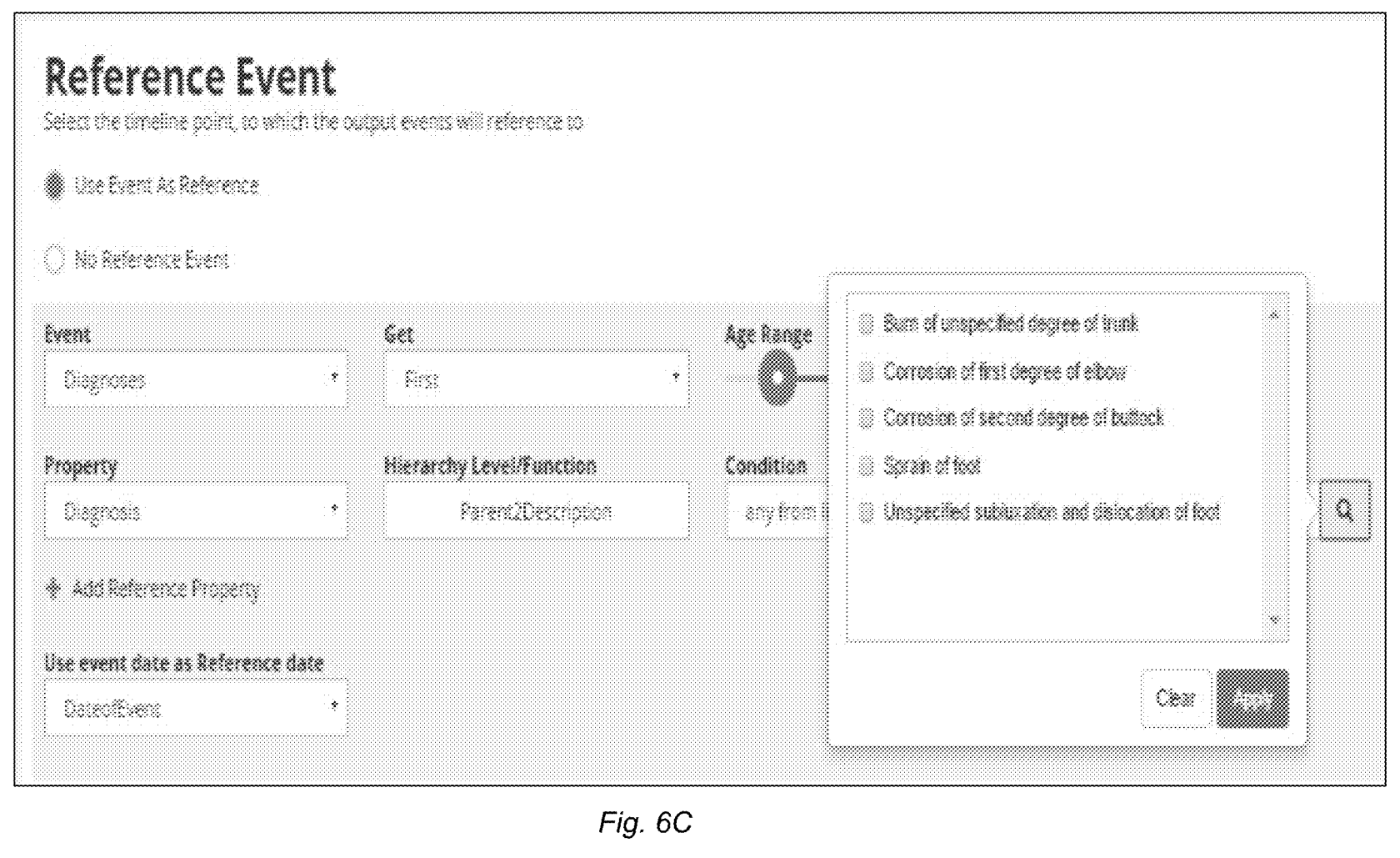

FIG. 6C shows another screenshot of another computer interface that the exemplary specially programmed inventive computing system may cause to be displayed to the exemplary user such that the user may be allowed to, for example but not limited, identify one or more reference events for the exemplary inventive real-time electronic negotiation querying session.

As referenced herein, the term "reference event" identifies, at a particular common time period, an arbitrary common event which is necessarily associated with a group of individuals whose the inventive synthetic non-reversible electronic data records the exemplary user desires to obtain. For example, in some embodiments, an exemplary reference event may be, but not limited to, spraining of a foot at age of 25.

As used herein, the term "non-reversible" identifies an inability to determine whether a particular piece of information is related to a particular individual.

In some embodiments, the inventive SNR EMRs have the same or suitability similar statistical characteristics as the source/original electronical medical records (EMRs) on the basis of which the inventive SNR EMRs have been generated by the inventive specially programmed computing systems. In some embodiments, the SNR EMRs are configured to avoid a risk of exposing private and/or confidential individual information.

Figure 6D:
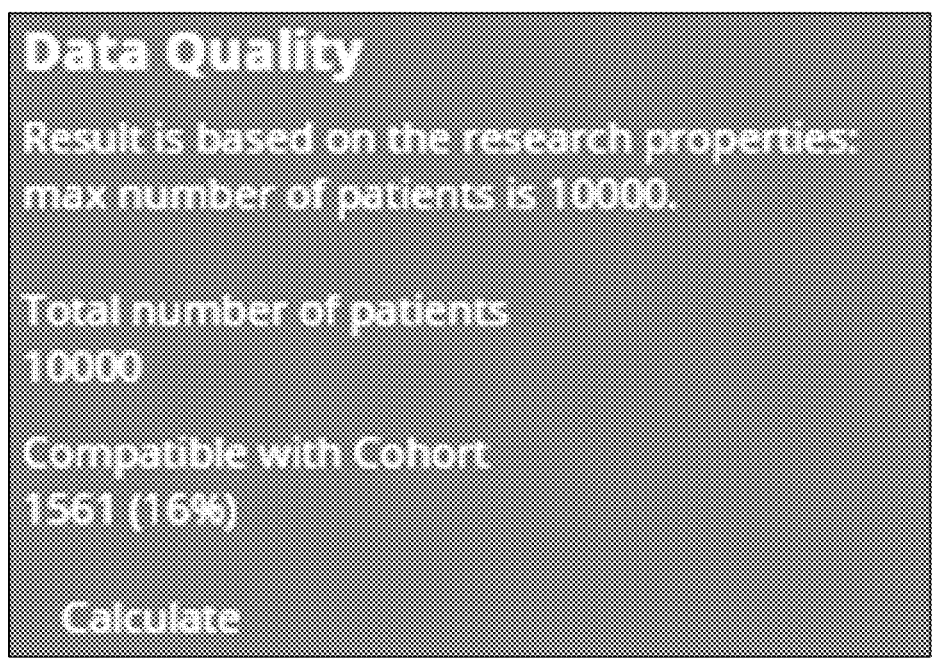

FIG. 6D shows another screenshot of another computer interface that the exemplary specially programmed inventive computing system may cause to be displayed to the exemplary user such that the user may be informed in real-time that, based on particular reference event(s) selected, how many individuals are being matched (e.g., "1561") from a total number of individuals (e.g., "10,000") for whom there would be EMRs in particular electronic source(s).

Figure 6E:
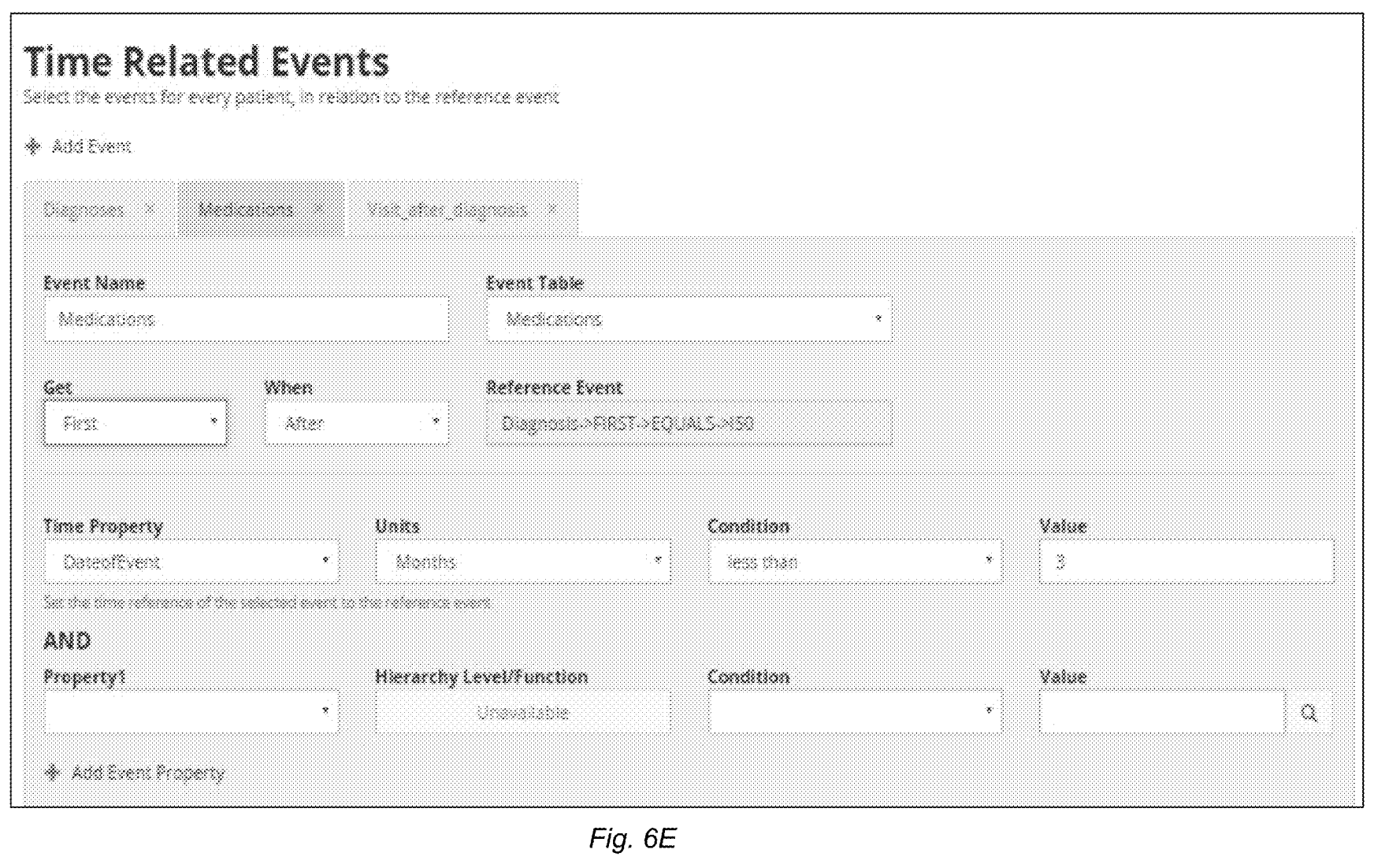

FIG. 6E shows another screenshot of another computer interface that the exemplary specially programmed inventive computing system may cause to be displayed to the exemplary user such that the user may further continue to define time-related properties (subevents) of one or more reference events to further define the desired population of individuals (i.e., defining the desired granularity of data).

Figure 6F:
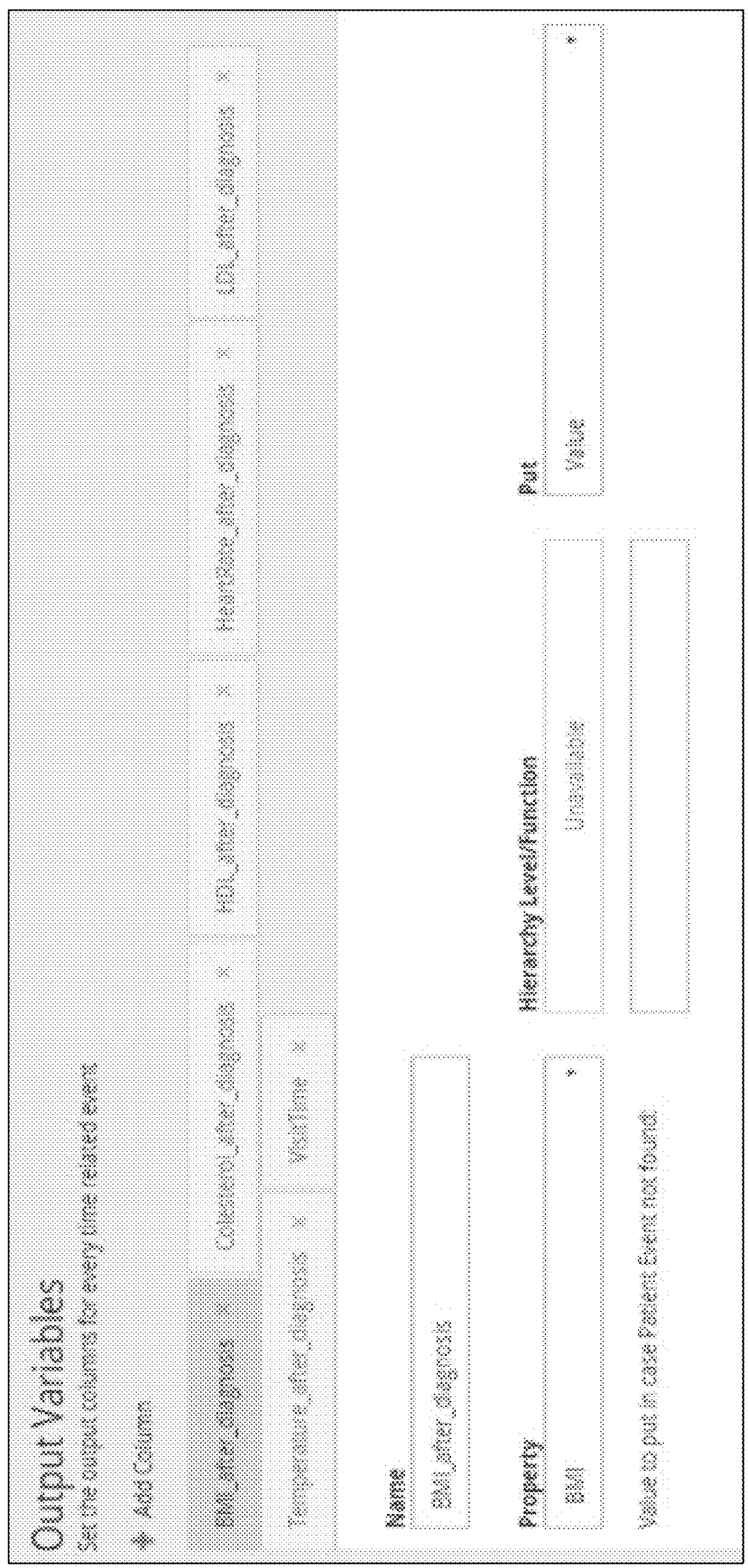

FIG. 6F shows another screenshot of another computer interface that the exemplary specially programmed inventive computing system may cause to be displayed to the exemplary user such that the user may further define output variable for each time-related property (subevent) of one or more reference events.

Figure 6G:
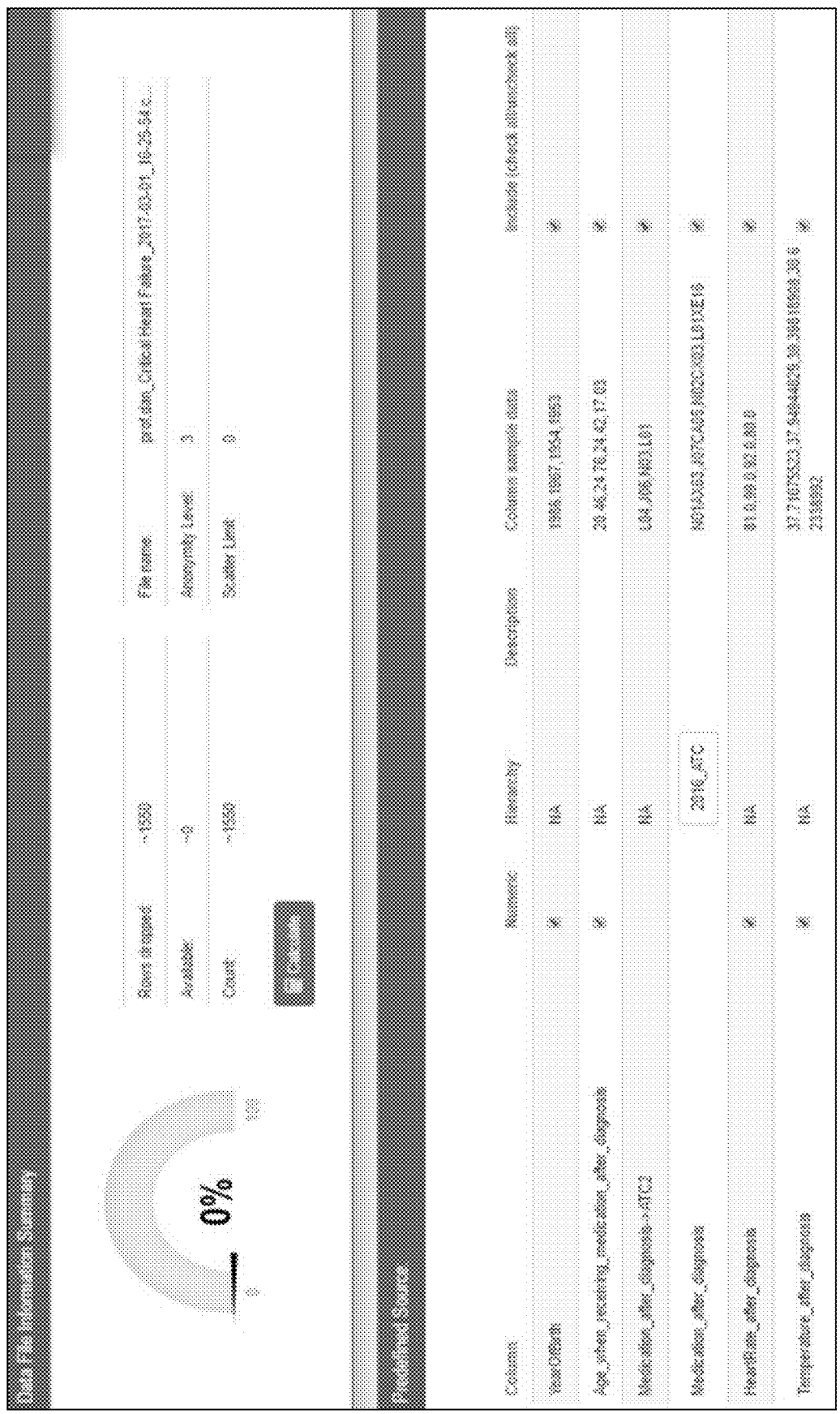

FIG. 6G shows another screenshot of another computer interface (a negotiation dashboard screen) that the exemplary specially programmed inventive computing system may cause to be displayed to the exemplary user such that the user may be informed that, based on negotiation parameters selected and the user's Anonymity Level of 3, there would be no records that match the user's selection.

Figure 6H:
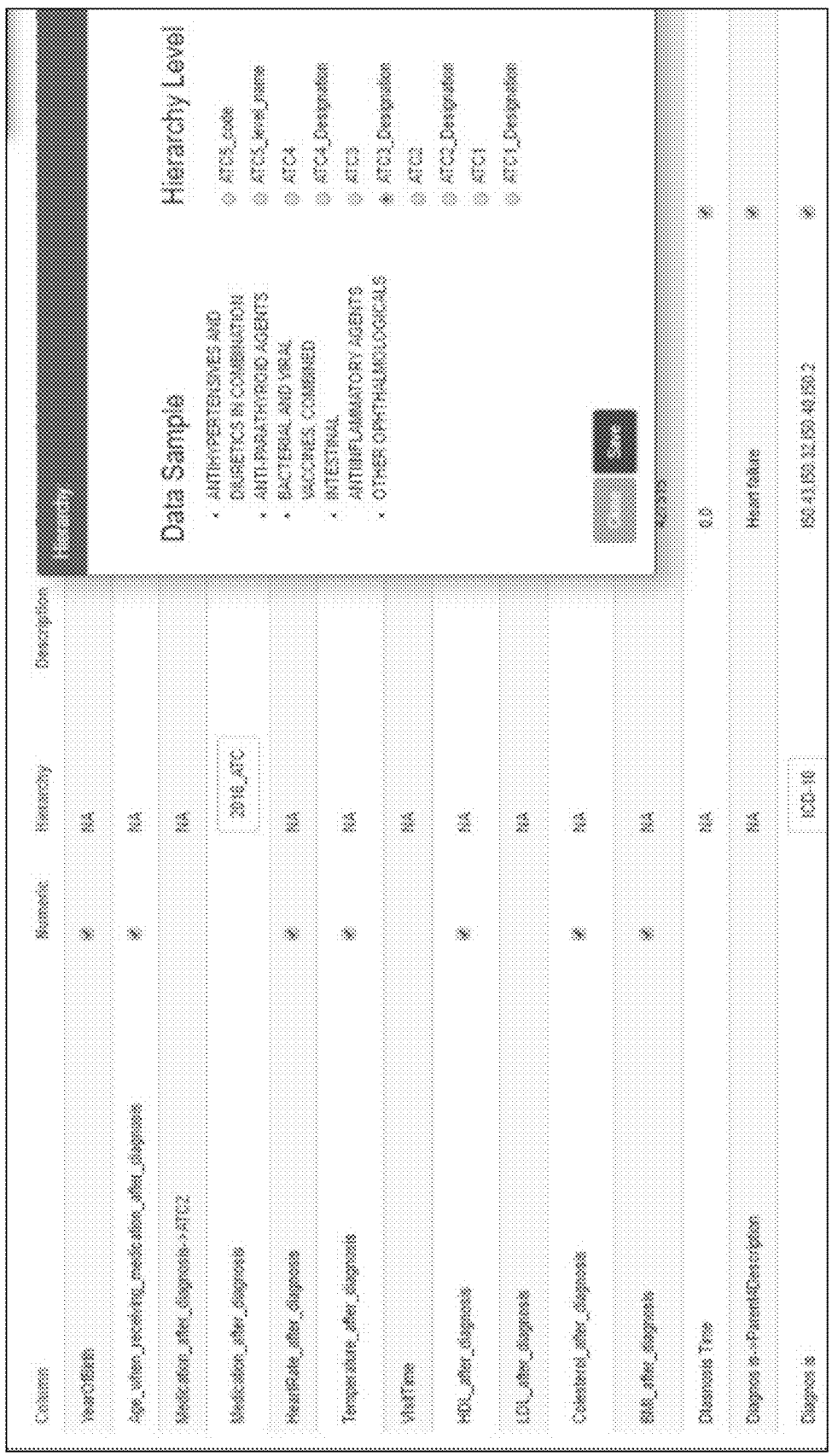
Figure 6I:
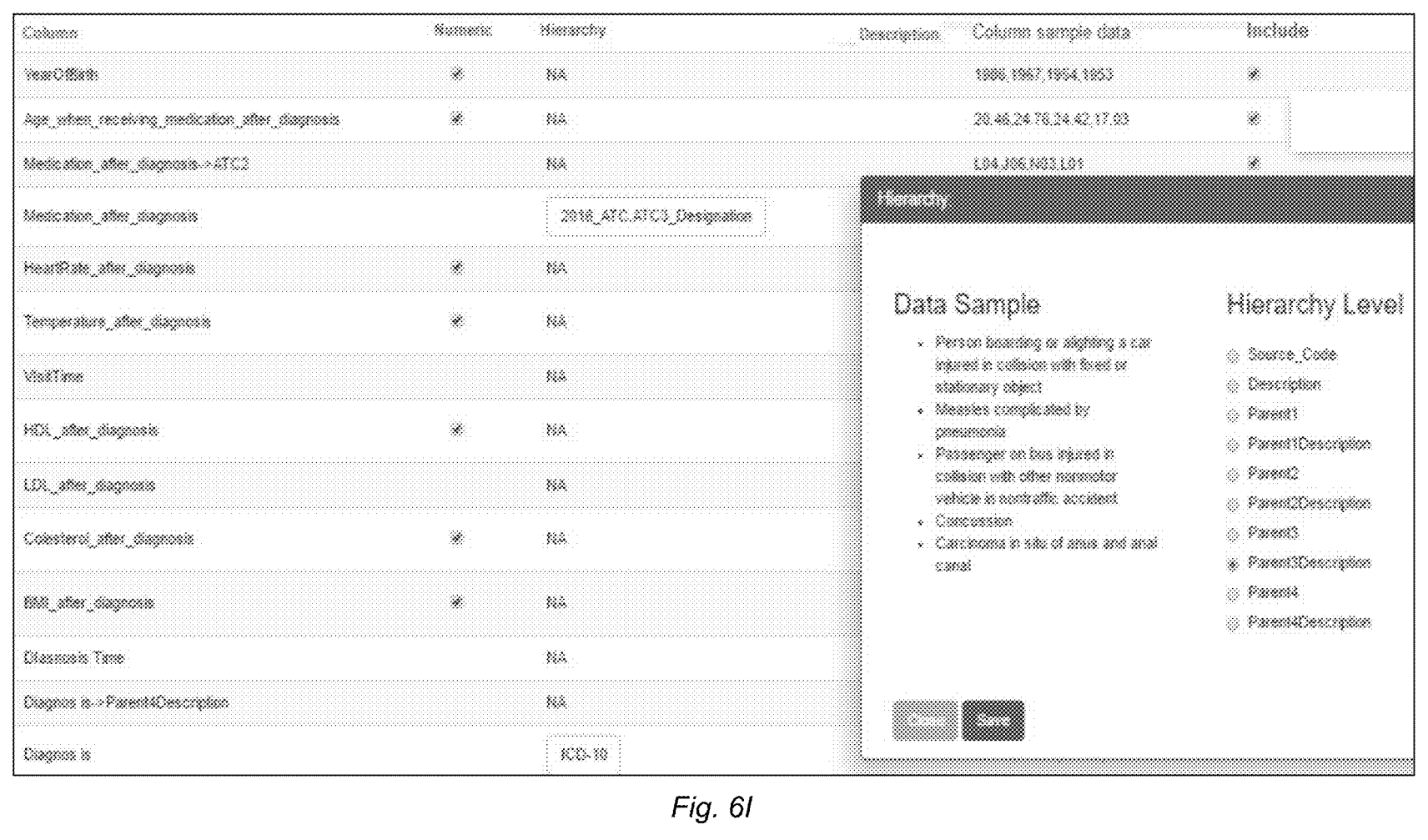

FIGS. 6H and 6I show screenshots of exemplary computer interfaces that the exemplary specially programmed inventive computing system may cause to be displayed to the exemplary user such that the user may change previously defined negotiation parameters to determine if the exemplary inventive computing system may determine that, based on the user's Anonymity Level, the user can receive some data. For example, utilizing the negotiation dashboard screen (FIG. 6G), the user can determine how change in a value of a particular negotiation parameter would affect a number of individuals for whom the data would be available.

Figure 6K:
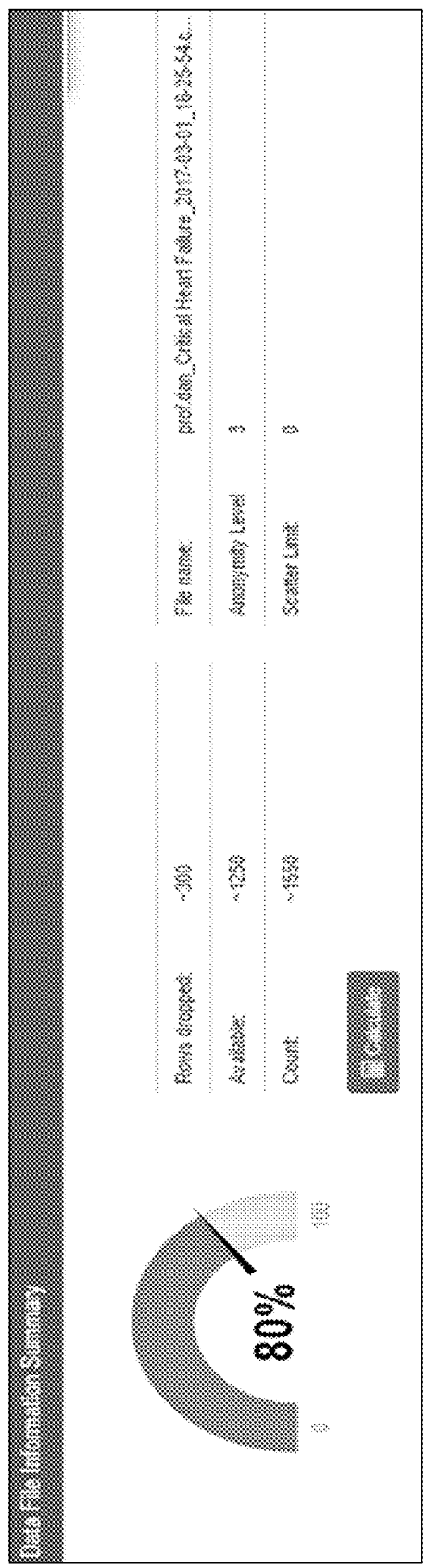

For example, after the user has changed the negotiation paramers as shown in FIGS. 6H and 6I, the negotiation dashboard screen shows, in FIG. 6K, that there would be records ("1250") that match the user's selection.

Figure 6L:
Figure 7C:
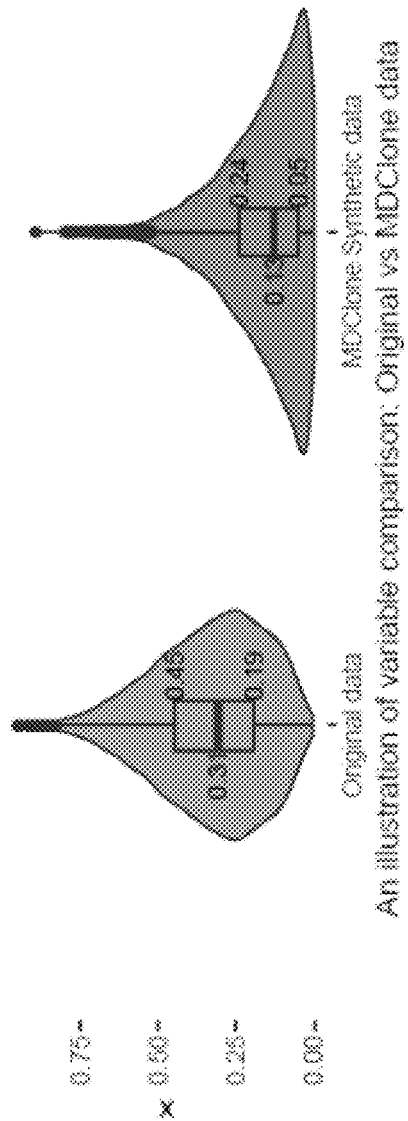
FIGS. 7A-8 show some exemplary aspects of the present invention in accordance with at least some principles of at least some embodiments of the present invention.
Figure 7D:
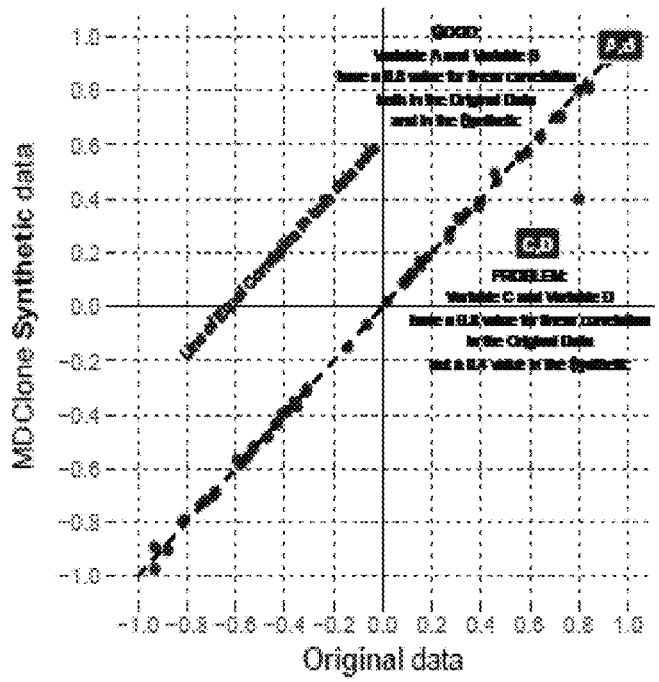
Figure 7E:
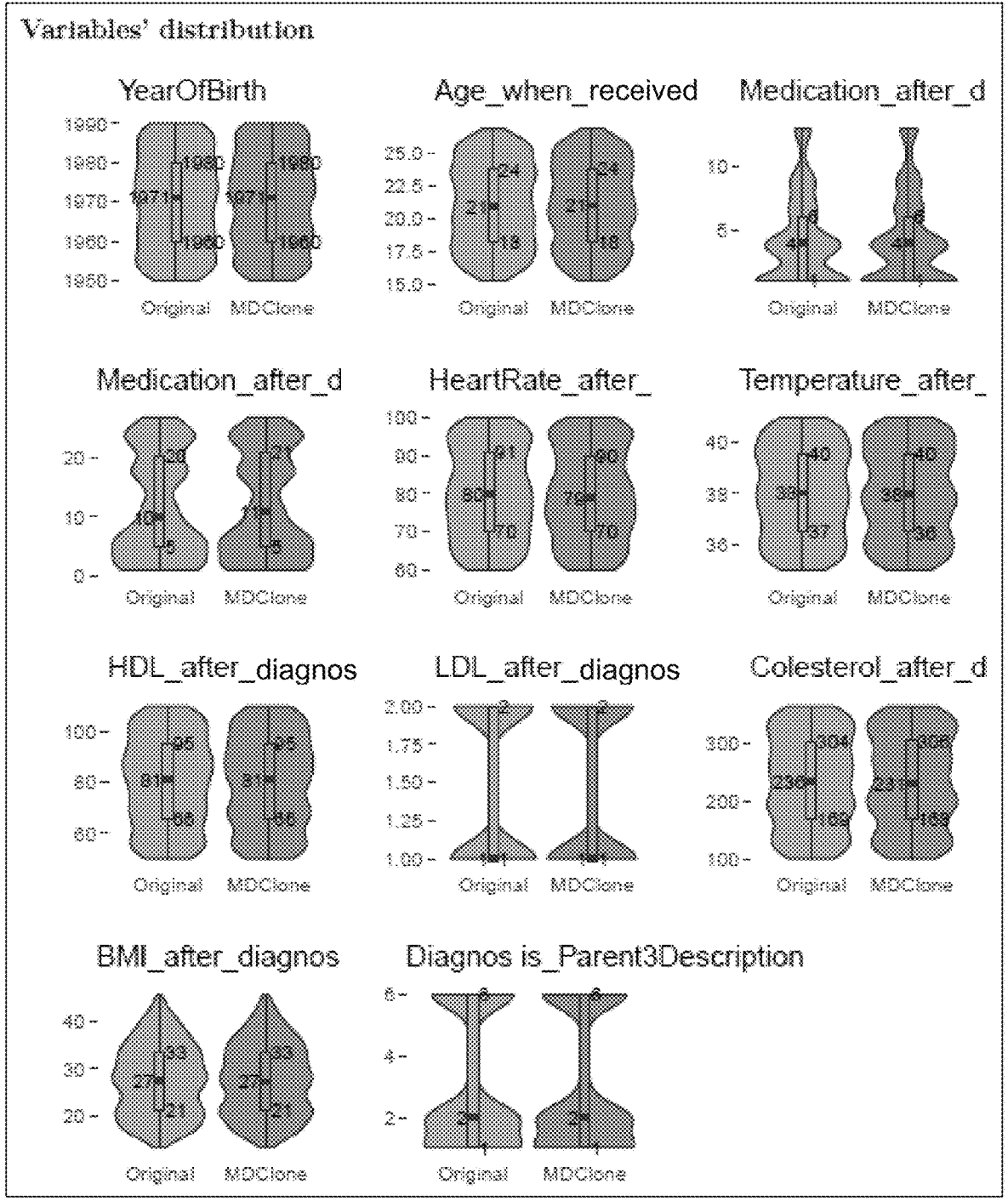
Figure 7F:
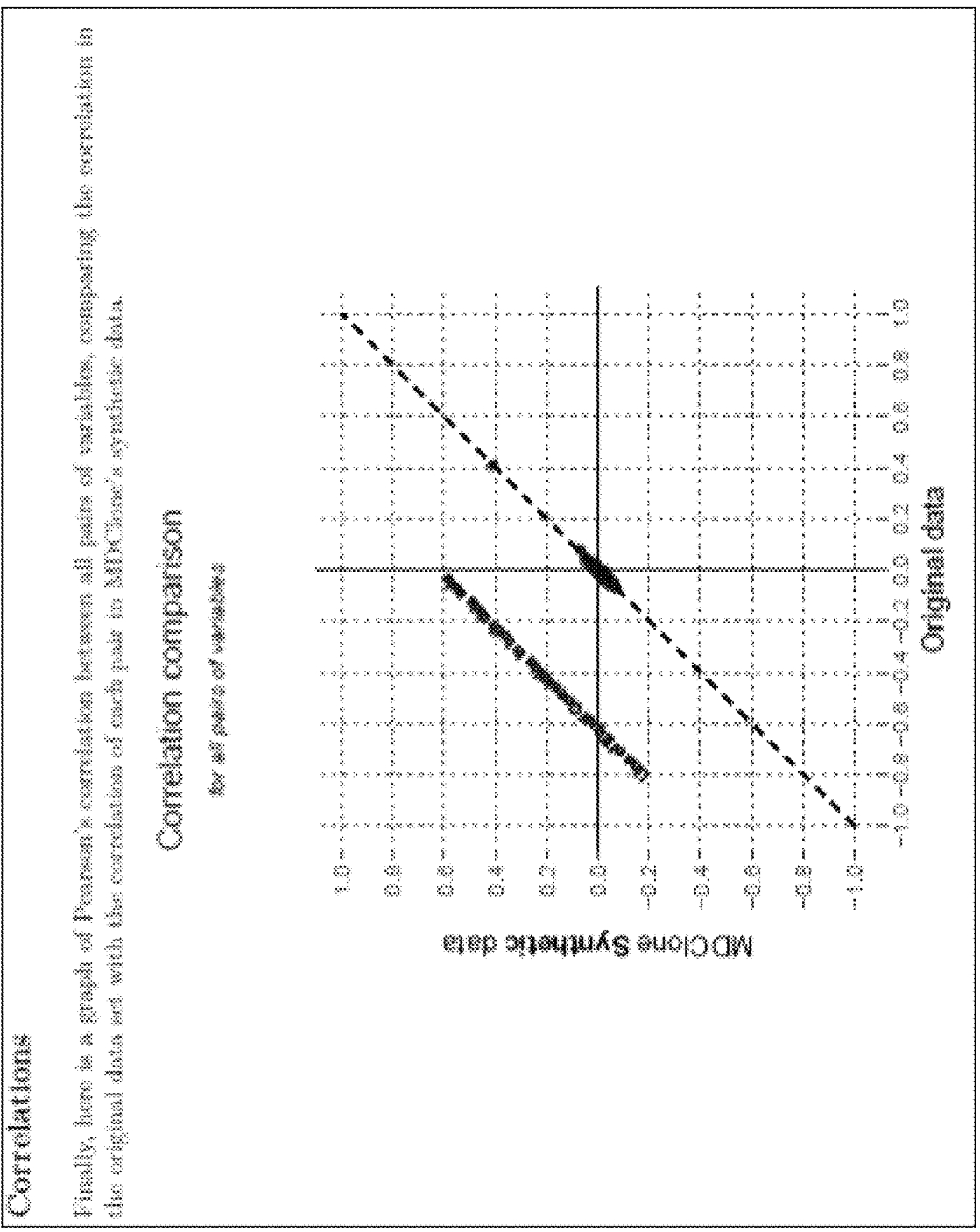

FIG. 6L shows another screenshot of another computer interface that the exemplary specially programmed inventive computing system may cause to be displayed to the exemplary user such that the user may select to download a file with the inventive SNR EMRs and/or obtain a comparison report that would statistically compare the source EMRs, which matched user's desired parameters, with the inventive SNR EMRs that have been generated by the exemplary specially programmed inventive computing system, where one would not be able to identify a single individual related to the source EMRs from the inventive SNR EMRs.

Figure 6M:
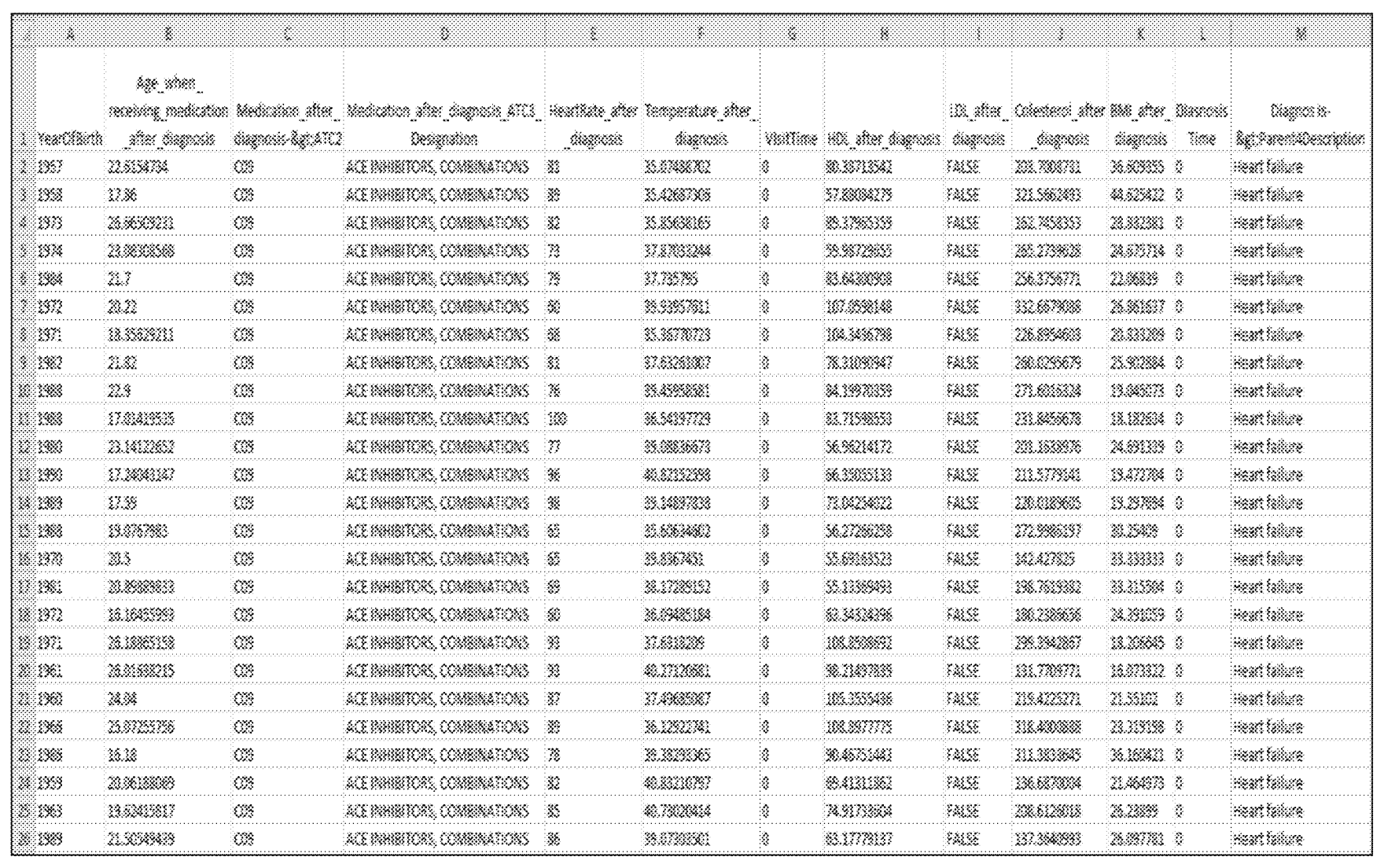

FIG. 6M shows a snapshot of a part of an Excel file generated by the exemplary specially programmed inventive computing system after the user would click on a Download Synthetic File button shown in FIG. 6L.

FIGS. 7A-7F show screenshots of an exemplary comparison report between the source EMRs, which matched user's desired parameters, with the inventive SNR EMRs that have been generated by the exemplary specially programmed inventive computing system. In some embodiments, the exemplary comparison report was generated by the exemplary specially programmed inventive computing system after the user would click on an Open Comparison Report button shown in FIG. 6L. As explanations shown in screenshots of the exemplary comparison report (FIGS. 7A-7F) explain that the exemplary comparison report allows the user to determine how statistically comparable the inventive SNR EMRs are to the source EMRs, and identifies what value(s) the user may need to adjust to achieve a sufficient level of statistical comparability.

Exemplary Embodiments of the Inventive Methods of Generating the Inventive SNR EMRs which are HIPAA Self-Compliant Under "the Expert Determination" Method Due to Avoidance of any Statistical Risk of the De-Identification (i.e., being Non-Reversible)

I. Background of HIPAA's Compliance

HIPAA is the Health Insurance Portability and Accountability Act of 1996 which is the U.S. federal law that sets rules about who can look at and receive health information of a particular individual. For example, HIPAA's compliant electronic management would need to be compliant with Privacy Rule as detailed in 45 C.F.R. Part 160 and Part 164, Subparts A and E, issued the U.S. Department of Health and Human Services. Under the HIPAA Privacy Rule, there are two ways that health information can be de-identified and therefore no longer considered Protected Health Information (PHI).

The first way of complying with the HIPAA Privacy Rule is to remove all 18 listed de-identification identifiers (the so-called "safe harbor" method). For example, the following de-identification identifiers of the individual or of relatives, employers, or household members of the individual to be removed are: (A) Names; (B) All geographic subdivisions smaller than a State, including street address, city, county, precinct, zip code, and their equivalent geocodes, except for the initial three digits of a zip code if, according to the current publicly available data from the Bureau of Census (1) the geographic units formed by combining all zip codes with the same three initial digits contains more than 20,000 people; and (2) the initial three digits of a zip code for all such geographic units containing 20,000 or fewer people is changed to 000; (C) All elements of dates (except year) for dates directly related to the individual, including birth date, admission date, discharge date, date of death; and all ages over 89 and all elements of dates (including year) indicative of such age, except that such ages and elements may be aggregated into a single category of age 90 or older; (D) Telephone numbers; (E) Fax numbers; (F) Electronic mail addresses: (G) Social security numbers; (H) Medical record numbers; (I) Health plan beneficiary numbers; (J) Account numbers; (K) Certificate/license numbers; (L) Vehicle identifiers and serial numbers, including license plate numbers; (M) Device identifiers and serial numbers; (N) Web Universal Resource Locators (URLs); (0) Internet Protocol (IP) address numbers; (P) Biometric identifiers, including finger and voice prints; (Q) Full face photographic images and any comparable images; and/or any other unique identifying number, characteristic, or code, except as permitted for re-identification purposes provided certain conditions are met.

The "safe harbor" method is not part of the present invention.

II. Exemplary Embodiments of the Inventive Methods of Generating the Inventive SNR EMRs which are HIPAA Self-Compliant Under "the Expert Determination" Method Due to Avoidance of any Statistical Risk of the De-Identification (i.e., being Non-Reversible)

The second way of complying with the HIPAA Privacy Rule is to obtain confirmation from a qualified statistician that the risk of identification is very small (the "expert determination" method)—the present invention meets this requirement based on the inventive SNR EMRs being HIPAA self-compliant since, as detailed herein, the present invention utilizes statistical methodologies that avoid any statistical risk of the de-identification (i.e., the inventive SNR EMRs being non-reversible).

For example, the inventive SNR EMRs is configured to be HIPAA compliant while representing the statistical characteristics of source EMRs which have been utilized to generate the inventive SNR EMRs. In some embodiments, an exemplary specially programmed computing system is configured to generate the inventive SNR EMRs based on and statistical data gathered from source EMRs data. In some embodiments, the inventive SNR EMRs contain precise numerical/quantitative information.

In some embodiments, an exemplary specially programmed inventive computing system can utilize various types of computing devices, such as, but not limited to, specially programmed Pearson correlational computer(s), specially programmed server(s), and similar others.

In some embodiments, the exemplary specially programmed inventive computing system is configured to process the source EMRs data objects which can include at least two types of data objects:

1) discrete data objects (e.g., gender, state, race, etc.); and 2) numeric/quantitative data objects (e.g., blood test results, exact age, etc.).

In some embodiments, the exemplary specially programmed inventive computing system is configured to extract statistical pattern(s)s from the source EMR data set(s) (1). In some embodiments, the source EMR data sets may be stored in at least one database of relational and/or NoSQL nature. For example, in some embodiments, at least one statistical representation of the source EMR data object is created in the RAM (Random Access Memory) of a computing device through a data transportation method, such as, but not limited to, a bulk data transfer protocol. In some embodiments, the exemplary specially programmed inventive computing system may be configured to utilize the at least one statistical representation to then create exemplary inventive SNR EMR(s). In some embodiments, the exemplary inventive SNR EMR(s) may be stored in a separate database of relational and/or NoSQL nature, on a file server as file(s), and/or in any other similarly suitable non-transient computer medium.

In some embodiments, the exemplary specially programmed inventive computing system is configured to utilize at least one three dimensional cell structure to analyze the source EMR data.

In some embodiments, the exemplary specially programmed inventive computing system is configured to utilize at least one flat table to analyze the source EMR data, reducing the source EMR data's dimensions to at least one two dimensional flat table structure. For example, in such embodiments, the at least one two dimensional flat table structure this table every row represents a single individual EMRs dataset, and every column represents a fact or a value related to a particular individual. For example, Table 1 provides an illustrative example of a data set that lists individuals who have a specific illness at specific data times.

TABLE 1

| Categorical Value Smoker | Categorical Value State | Categorical Value Gender | Numeric Value Cholesterol | Numeric Value HDL | Numeric Value LDL |
|---|---|---|---|---|---|
| yes | FL | Male | 107 | 38 | 38 |
| no | NJ | Female | 145 | 43 | 21 |
| yes | NJ | Male | 132 | 45 | 27 |
| yes | NJ | Male | 132 | 33 | 37 |
| yes | NJ | Male | 122 | 87 | 33 |
| no | NY | Female | 122 | 56 | 55 |
| yes | TX | Male | 132 | 89 | 42 |
| no | CL | Female | 132 | 33 | 37 |
| yes | CL | Male | 134 | 56 | 55 |
| no | TX | Male | 145 | 89 | 42 |
| yes | TX | Male | 132 | 33 | 37 |
| no | NY | Male | 134 | 56 | 55 |
| yes | AL | Male | 132 | 45 | 27 |
| no | AK | Female | 134 | 87 | 33 |
| yes | CT | Male | 107 | 38 | 38 |
| yes | AL | Male | 132 | 33 | 37 |
| yes | AK | Male | 107 | 38 | 38 |
| no | NY | Female | 107 | 38 | 38 |
| yes | AL | Male | 145 | 89 | 42 |
| no | AK | Female | 122 | 56 | 55 |
| yes | CT | Male | 122 | 87 | 33 |
| no | AL | Male | 134 | 87 | 33 |
| yes | AK | Male | 145 | 45 | 27 |
| no | CT | Female | 132 | 89 | 42 |

For example, a typical source EMR dataset can have at least 1,000 to 1,000,000 rows and at least 50 to 1,000 columns. For example, a typical source EMR dataset can have at least 10,000 to 1,000,000 rows and at least 100 to 2,000 columns. For example, a typical source EMR dataset can have at least 1,000 to 10,000,000 rows and at least 50 to 3,000 columns. For example, a typical source EMR dataset can have at least 10,000 to 1,000,000,000 rows and at least 50 to 3,000 columns. For example, a typical source EMR dataset can have at least 1,000 rows and at least 50 columns. For example, a typical source EMR dataset can have at least 10,000 rows and at least 100 columns. For example, a typical source EMR dataset can have at least 1,000,000 rows and at least 100 columns. For example, a typical source EMR dataset can have at least 1,000 rows and at least 1,000 columns. For example, a typical source EMR dataset can have at least 10,000 rows and at least 2,000 columns. For example, a typical source EMR dataset can have at least 1,000,000 rows and at least 2,000 columns.

For purposes of illustration only, as shown in Table 1, one exemplary source EMR contains 3 categorical values columns, 3 numerical values columns and records for 23 individuals. For example, another exemplary source EMR can represent hundreds of additional parameters, such as, but not limited to, Body-to Mass Index (BMI), height, Prostate Screen Analysis (PSA) result, glucose level, average blood pressure in the last 3 months, etc. For example, as detailed herein, an exemplary source EMR data object may contain records for at least one thousand individuals.

Illustrative Examples of Various Anonymity Levels

In some embodiments, the exemplary specially programmed inventive computing system is configured to engage a user in the real-time electronic negotiation querying based, at least in part, on an anonymity level associated with such user. In some embodiments, the exemplary specially programmed inventive computing system may dynamically assign, in real-time, a particular anonymity level to the user based on one or more characteristic of the user. In some embodiments, the particular anonymity level is related to a minimum size of a population group having at least one particular patient/personal event and/or demographic property. In some embodiments, the exemplary specially programmed inventive computing system is configured to utilize any suitable combination of distinct pieces of data related to the population group to determine the minimum size corresponding to the particular anonymity level.

In some embodiments, the exemplary specially programmed computing system configured to output the inventive SNR EMRs only when a value of the user's associated anonymity level for at least one desired data characteristic profile is equal or smaller to a number of individuals with identical set of values in the source EMR. For example, in some embodiments, the exemplary specially programmed computing system configured to utilize the anonymity levels to determine the level of access to the source EMR via the inventive SNR EMRs for various types of users. In some embodiments, the exemplary specially programmed inventive computing system is configured to assign a particular anonymity level to a user when the user registers with the exemplary specially programmed inventive computing system. In some embodiments, the exemplary specially programmed inventive computing system is configured to modify the anonymity level access based on the user's relationship to the source EMRs.

For example, a typical access level for a medical staff member (with the assumed access to actual medical records) of a medical institution, where the source EMR is stored at the same locale associated with the medical staff member, can be set at a low anonymity level, such as, but not limited to, 2 or 3 (e.g., the anonymity level can be based on an arbitrary numerical scale). For example, the exemplary specially programmed computing system is configured to associate an outside user (e.g., the medical staff member of the medical institution, assessing over an external communication connection, an external user who is not a medical staff member) with a high anonymity level (e.g., 8-10). For example, the outside user's anonymity level of 10 signifies that the exemplary specially programmed computing system is configured to prevent such outside user from receiving the inventive SNR EMRs which corresponds to knowledge of information which can related directly to less than 10 individuals.

In some embodiments, as part of the inventive real-time electronic negotiation querying, based on the anonymity level value, the exemplary specially programmed computing system is configured to remove any combination of categorical values and/numerical values that is less than the given number of individual records in the source EMR from being part of the inventive SNR EMRs when the inventive SNR EMRs being generated.

For example, with the reference to the illustrative example of the source EMR of Table 2, assuming that the exemplary specially programmed computing system has assigned an anonymity level of 3 to a particular user. As detailed above, Table 1 has 3 categorical value columns of: "Smoker," "State," and "Gender." As Table 1 shows, there are 3 smoking male individuals in NJ (the anonymity level of 3 equals to having at least 3 individuals) whose records can be used by the exemplary specially programmed computing system to the inventive SNR EMR datasets from the source EMR datasets.

However, as Table 1 shows, there are only two non-smoker Female individuals in NJ (i.e., 2 non-smoker Female individuals<the anonymity level value of 3), hence the exemplary specially programmed computing system is configured to disregard the source EMR data of the two non-smoker Female individuals in NJ when generating the inventive SNR EMR datasets.

If the particular user still desires to extract information from the omitted records, during the inventive real-time electronic negotiation querying, the user can ask the exemplary specially programmed computing system to use a higher hierarchy (e.g., lower data granularity) of the source EMR dataset, and include those records in generating the inventive SNR EMR datasets. For example, in such case, the user may be satisfied with having the inventive SNR EMR datasets being generated, from the source EMR datasets, based on a region level as oppose to the state level. In such example, the exemplary specially programmed computing system is configured to represent values for NY and NJ individuals in combination as "East Coast" data. Since, as Table shows, there are 4 non-smokers Females on the East Coast (2 in NY and 2 in NJ), the combined records result in 4 records being more that the anonymity value of 3. Consequent, based on such level of representation (i.e., "East Coast" level), the exemplary specially programmed inventive computing system will include the source data of such individuals when generating the exemplary inventive SNR EMR(s).

For example, as another option to be explored during the inventive real-time electronic negotiation querying, the user may decide not to receive information in the field "Smoker"—i.e., setting the value for this categorical column to a higher hierarchy (e.g., "All"=Smokers and non-Smokers). In such case, there are 4 people in New Jersey, allowing the exemplary specially programmed inventive computing system to include the source data of such individuals when generating the exemplary inventive SNR EMR(s).

In some embodiments, the exemplary specially programmed inventive computing system is configured to next fill all the discrete columns by using, for example but not limited to, a conditional probability methodology which can include the following steps. In some embodiments, the exemplary specially programmed inventive computing system is configured to apply the anonymity level for the discrete columns only and apply the self-recalculation method for the numeric columns.

Step 1: Colum-by-Column Self-Transformation for Columns with Categorical Values

In some embodiments, the exemplary specially programmed inventive computing system is configured to randomize values for the first column based on the distribution of the items on the original data set for the first column. For example, in Table 1, there are 10 non-smokers and 14 smokers. This leads to a ratio of 10/24 of non-smokers (or 41.6%) and a ratio of 14/24 of smokers (or 58.4%). At this stage, the exemplary specially programmed inventive computing system has values for only one column (Smokers—yes/no) that holds this ratio.

Then, in some embodiments, the exemplary specially programmed inventive computing system is configured to move to the next row and repeat the process. Similarly, the exemplary specially programmed inventive computing system may be configured to repeat the ratio calculation up to the number of the anticipated synthetic records. For example, at this stage, the first 10 records may retain the values shown in Table 2.

In some embodiments, the exemplary specially programmed inventive computing system is configured to proceed to the next (second) column. Similarly, the exemplary specially programmed inventive computing system is configured to randomize values for this column based on the distribution of the items on the original data set for this column, taken into account all previous data elements that has been created in the row. For example, if the row includes a non-smoker in NY by the randomization process, then the Gender probability would be ⅓ (33.33%) male and ⅔ (66.66%) female.

TABLE 2

| Smoker |
|---|
| yes |
| yes |
| yes |
| no |
| yes |
| yes |
| yes |
| no |
| no |
| yes |

In some embodiments, the exemplary specially programmed inventive computing system is configured to repeat the same process all the columns with categorical values in the original data set. For example, at this stage, the first 10 records of the exemplary inventive SNR EMR may retain the values shown in Table 3.

In some embodiments, after the exemplary specially programmed inventive computing system uses the conditional probability method, the exemplary specially programmed inventive computing system is configured to generate a new set of the inventive SNR EMRs for the categorical value data objects (not the numeric ones). At this stage, the number of inventive SNR EMRs in the new set may be equal to or larger than the number of the source EMRs.

TABLE 3

| Smoker | State | Gender |
|---|---|---|
| yes | AL | Male |
| yes | NJ | Male |
| yes | TX | Male |
| no | CL | Female |
| yes | AK | Male |
| yes | CT | Male |
| yes | FL | Male |
| no | NY | Male |
| no | NJ | Female |
| yes | AK | Male |

Step 2: Colum-by-Column Self-Transformation for Columns with Numeric Values

In some embodiments, the exemplary specially programmed inventive computing system is configured to generate an array of the dimension n×m, for every combination of the categorical value columns. In some embodiments, the exemplary specially programmed inventive computing system is configured to utilize the truncation of table objects. For example, the array is a matrix of numerical values of the dimension m, where m represents the columns (value/facts) and n represents the rows (a number of individuals per each combination). In one scenario, if in the combination of categorical values in a raw is Smokers="yes," State="NJ," and Gender="Male" and those are the only categorical value columns in the source EMR dataset, the exemplary specially programmed inventive computing system would identify 3 individuals and, if the numeric value columns would be HDL level and Cholesterol level, the exemplary specially programmed inventive computing system would have utilize a matrix P of 3×2, a total of 6 values. In Table 4, each cell of the n×m array, which the exemplary specially programmed inventive computing system would modify, is identified with an asterisk.

TABLE 4

| Smokers | State | Gender | Cholesterol | HDL |
|---------|-------|--------|-------------|-----|
| no      | FL    | Male   | 132         | 89  |
| no      | NJ    | Female | 122         | 87  |
| yes     | NJ    | Male   | 145*        | 45* |
| yes     | NJ    | Male   | 132*        | 33* |
| yes     | NJ    | Male   | 134*        | 56* |
| no      | NY    | Female | 107         | 38  |

In some embodiments, the exemplary specially programmed inventive computing system is configured to replace the matrix P with a new matrix T with minimum n×m dimensions, stored in a new array (2). For example, the values in the matrix T retain similar statistical characteristics as the values of the matrix P based, at least in part, on the following steps. For example, during the real-time negotiation, the exemplary specially programmed inventive computing system is configured to determine at least one statistical characteristic which needs to be conserved. In one scenario, in some embodiments, the exemplary specially programmed inventive computing system is configured to utilize one or more of the following equations to calculate a value of a particular statistical characteristic, but not being limited to.

Exemplary Average Equation $$\bar{x} = f_{Av(j)} = \frac{\sum_{i=1}^{n} x_i}{n}, \quad (1)$$

where $x_i$ is the value of column j individual i.

For example, in the above illustrative example (Smokers and NJ and males: n=3), the exemplary specially programmed inventive computing system would calculate the average value for the matrix T (HDL values) to be (45+33+56)/3=44.66.

Exemplary Standard Deviation Equation $$\sigma = f_{Sd(j)} = \sqrt{\frac{1}{n}\sum_{i=1}^{n}(x_i - \bar{x})^2} \quad (2)$$

In mathematics, a system of equations is considered underdetermined if there are fewer equations than unknowns. Each unknown can be seen as an available degree of freedom. Each equation introduced into the system can be viewed as a constraint that restricts one degree of freedom. Such a system will have an infinite number of solutions in the general case. In accordance with the principles of the present invention, due to the fact that the number of equations solved is smaller than the number of variables, there is an infinite combination of variables that will satisfy the set of equations. In some embodiments, the exemplary specially programmed inventive computing system of the present invention randomly selects from this infinite set a single set. Ones the data is given to the end user the only fact that the user can deduct about a specific person in the data set is that such person belongs to a group with no option to deduct such person's original data (i.e., there is no a known method to identify the original variable combination out of the infinite one).

For example, in the above illustrative example (Smokers and NJ and males: n=3), the exemplary specially programmed inventive computing system would calculate the standard deviation for the matrix T (HDL values) to be:

$$(((45 - 44.66)^2 + (33 - 44.66)^2 + (56 - 44.66)^2)/3)^{1/2} =$$

$$\sqrt{\frac{397}{3}} \approx 11.504$$

In some embodiments, the exemplary specially programmed inventive computing system is configured to utilize at least one pre-defined equation for every statistical characteristic and column intended to be conserved from the source EMR dataset, resulting in m equations per column based on desired characteristic (e.g., average, standard deviation, etc.).

For example, for each desired statistical characteristic involving two or more columns (such as, but not limited to, Pearson correlation), the exemplary specially programmed inventive computing system is configured to utilize an equation which would process any column permutations.

For example, in some embodiments, the exemplary specially programmed inventive computing system is configured to utilize the $$\frac{m(m-1)}{2}$$

equation for "m" desired numeric columns based on the Pearson correlation. Hence, in some embodiments, the exemplary specially programmed inventive computing system is configured to utilize the total number of equations which can be determined based on the $$\frac{m(m-1)}{2}l + km$$

equation, where "m" is a number of numeric columns, "l" is a number of statistical characteristics involving two columns (such as Pearson correlation), "k" is a number of characteristics related to a single column. For example, the total number of variables can be determined as a product of (m×n), where "m" is a number of numeric value columns, and "n" is a number of individuals for that combination. In the above scenario, if m=3 for the Pearson correlation-based transformation, the exemplary specially programmed inventive computing system is configured to solve 3×(3−1)/2=3 equations.

In another scenario, where there are less equations than a number of variables, determined as the product of (m×n), the exemplary specially programmed inventive computing system is configured to select/generate random values for "g" variables (g=number of variables−number of equations). In some embodiments, the exemplary specially programmed inventive computing system is configured to set each random value of a particular variable within a range of values suitable to the source EMR value (categorical/numerical). In some embodiments, the exemplary specially programmed inventive computing system is configured to populate a new matrix with "g" numeric values. In some embodiments, the exemplary specially programmed inventive computing system is configured to solve the system of equations for all the other variables in such a way as to satisfy all of the equations.

In another scenario, where there are more equations than the number of variables, the exemplary specially programmed inventive computing system is configured to generate additional fictitious record(s) where each fictitious record represents a synthetic individual (a particular inventive SNR EMR). In such case, in some embodiments, the exemplary specially programmed inventive computing system is configured to add/append the same proportional number of new records to all matrices. Then, in some embodiments, the exemplary specially programmed inventive computing system is configured to solve the system of equations for all the other variables in such a way that would satisfy all the equations.

Figure 8:
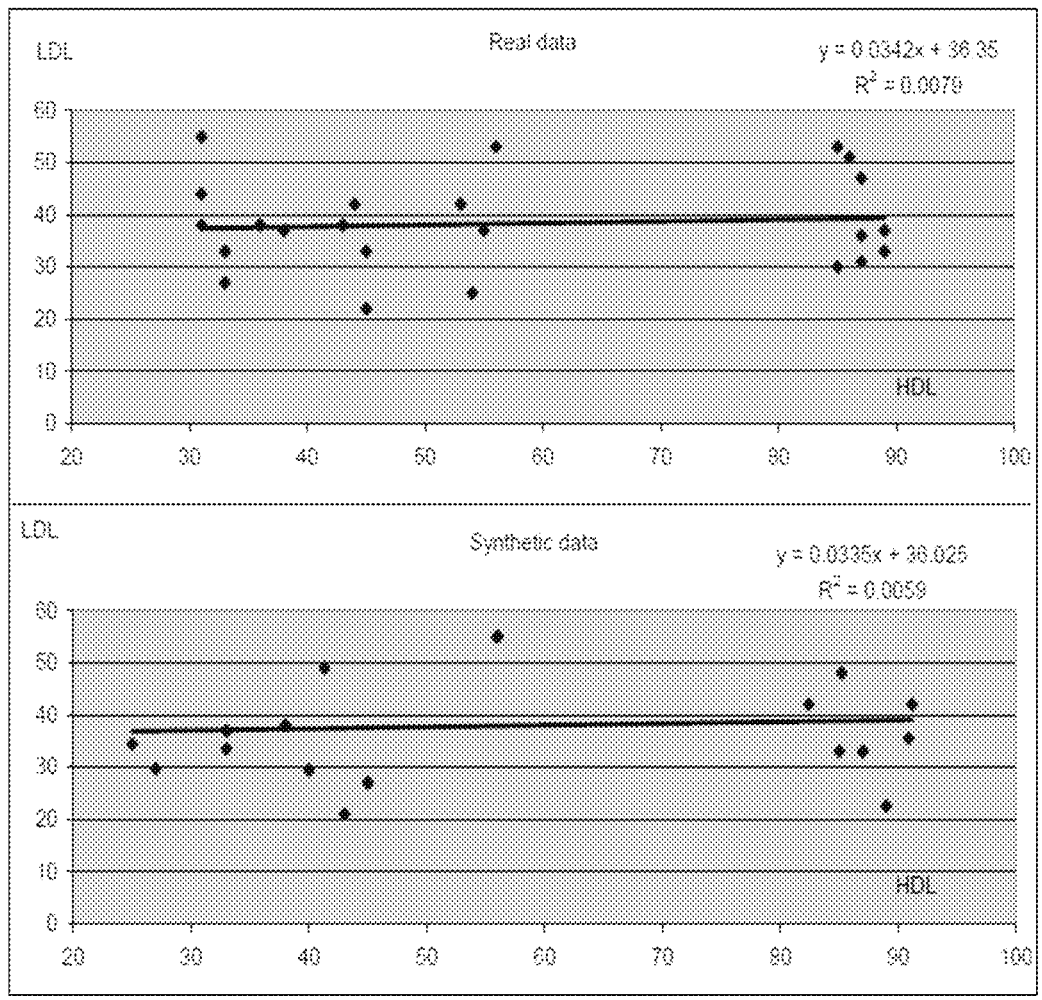

Table 5 illustrates illustrative inventive SNR EMRs data objects which the exemplary specially programmed inventive computing system would generate and store in the computer memory from the source EMRs of Table 1. For example, as Table 1 shows, the HDL average value for Table 1 (the source EMRs) is 58. As Table 5 illustrates, the HDL average value is 57.5 for the exemplary inventive SNR EMRs. As graphs in FIG. 8 illustrate, while Table 1 and Table 5 differ in values and dimensions, in case of utilizing the Pearson correlation to generate the exemplary inventive SNR EMRs, the Pearson correlation/Linear regression would be practically (sufficiently) the same.

In some embodiments, the exemplary specially programmed inventive computing system is configured to utilize the anonymity level screening for the self-transformation of columns with categorical values and utilize the recalculation method for columns with numerical values.

TABLE 5

| Smoker | State | Gender | Cholesterol | HDL | LDL |
|--------|-------|--------|-------------|-----|-----|
| yes | AK | Male | 145 | 45 | 21 |
| no | AK | Female | 122 | 56 | 27 |
| yes | AL | Male | 132 | 33 | 27 |
| no | AK | Female | 134 | 87 | 28 |
| no | AL | Male | 132 | 87 | 31 |

TABLE 5-continued

| Smoker | State | Gender | Cholesterol | HDL | LDL |
|--------|-------|--------|-------------|-----|-----|
| yes | TX | Female | 132 | 45 | 33 |
| yes | AL | Male | 145 | 89 | 33 |
| no | CL | Female | 132 | 33 | 33 |
| yes | NY | Male | 122 | 87 | 36 |
| yes | CL | Male | 142 | 56 | 37 |
| yes | CT | Male | 107 | 38 | 37 |
| no | CT | Female | 132 | 89 | 37 |
| yes | AK | Male | 107 | 38 | 38 |
| yes | FL | Male | 107 | 38 | 38 |
| yes | NJ | Male | 132 | 33 | 38 |
| no | NJ | Female | 145 | 43 | 38 |
| yes | NJ | Male | 166 | 45 | 42 |
| yes | AK | Male | 122 | 87 | 42 |
| no | NY | Female | 122 | 56 | 42 |
| no | NY | Male | 107 | 31 | 44 |
| yes | TX | Male | 132 | 89 | 51 |
| no | NY | Female | 134 | 56 | 55 |
| yes | TX | Male | 132 | 33 | 55 |
| no | TX | Male | 145 | 88 | 55 |

In some embodiments, the present invention provides for an exemplary computer system which includes at least the following components: at least one graphical user interface client; at least one dedicated application server; where the at least one dedicated application server at least includes: a non-transitory memory storing instructions and at least one server processor; where, when executing the instructions by the at least one server processor, the at least one dedicated application server is configured to operationally connect to the at least one graphical user interface client and at least one electronic source with a plurality of electronic data records; where the plurality of electronic data records includes at least 10,000 data records; where the plurality of electronic data records includes real identification identifiers of real individuals; where the at least one graphical user interface client is configured to utilize at least one processor of a computing device of a user to: generate at least first graphical user interface that includes: i) at least one first programmable software object which is configured to receive user authenticating credential information; where the at least one dedicated application server is configured to assign an anonymity level to the user based on user authenticating credential information; ii) a plurality of second programmable software objects which are configured to conduct at least one real-time electronic negotiation querying session between the user and the at least one dedicated application server; where the at least one real-time electronic negotiation querying session is configured to: 1) receive, from the user, via the plurality of second programmable software objects, at least the following: a) at least one of: a plurality of personal event data parameters of at least one personal event and at least one demographic identifier, and b) a plurality of reference event data parameters of at least one reference event, where the plurality of reference event data parameters of the at least one reference event include a plurality time-related property data parameters for at least one time-related property of the at least one reference event; 2) allow, the user, via the plurality of second programmable software objects, to iteratively adjust the plurality of personal event data parameters of the at least one personal event and at least one of the at least one demographic identifier and the plurality of reference event data parameters of the at least one reference event so that, based on the anonymity level of the user, there is a matched subset of a minimal number of real individuals associated with the plurality of electronic data records of the at least one electronic source match the at least one personal event and the at least one reference event; 3) display, in real-time, an indication of how many real individuals are in the matched subset; 4) generate, with each adjustment iteration, a plurality of non-reversible synthetic electronic data records of a plurality of synthetic individuals, by utilizing at least one statistical technique to perform at least one of: self-recalculation of discrete values of the plurality of electronic data records of the matched subset and self-transformation categorical values of the plurality of electronic data records of the matched subset; and 5) electronically output, for the user, the plurality of non-reversible synthetic electronic data records of the plurality of synthetic individuals to at least one electronic destination associated with the user; and where the plurality of non-reversible synthetic electronic data records of the plurality of synthetic individuals: a) are statistically representative of the matched subset, b) have at least one synthetic identification identifier corresponding to at least one real identification identifier of a real individual from the matched subset, and c) cannot be utilized to identify any real individual from the matched subset.

In some embodiments, the at least one dedicated application server is configured to assign the anonymity level to the user based on an entity affiliation of the user.

In some embodiments, the at least one statistical technique is a conditional probability methodology.

In some embodiments, the at least one real-time electronic negotiation querying session is further configured to generate at least one comparison report, analyzing all pairs of variables between the plurality of electronic data records of the matched subset and the plurality of non-reversible synthetic electronic data records of the plurality of synthetic individuals.

In some embodiments, the at least one comparison report is generated based on pearson's correlation for each pairs of variables between the plurality of electronic data records of the matched subset and the plurality of non-reversible synthetic electronic data records of the plurality of synthetic individuals.

In some embodiments, the plurality of electronic data records are a plurality of electronic medical records. In some embodiments, the plurality of non-reversible synthetic electronic data records of the plurality of synthetic individuals are HIPAA self-compliant. In some embodiments, the at least one synthetic identification identifier is de-identification identifier which is required, based on HIPAA, to be removed from the plurality of electronic data records of the matched subset prior to being outputted to the at least one electronic destination associated with the user.

In some embodiments, the present invention provides for an exemplary computer system which includes at least the following steps: causing to install at least one graphical user interface client on a computing device of a user; where the at least one graphical user interface client is configured to operationally connect to at least one dedicated application server; where the at least one dedicated application server includes: a non-transitory memory storing instructions and at least one server processor; where, when executing the instructions by the at least one server processor, the at least one dedicated application server is configured to operationally connect to the at least one graphical user interface client and at least one electronic source with a plurality of electronic data records; where the plurality of electronic data records includes at least 10,000 data records; where the plurality of electronic data records includes real identification identifiers of real individuals; where the at least one graphical user interface client is configured to utilize at least one processor of the computing device of the user to: generate at least first graphical user interface that includes: i) at least one first programmable software object which is configured to receive user authenticating credential information; where the at least one dedicated application server is configured to assign an anonymity level to the user based on user authenticating credential information; ii) a plurality of second programmable software objects which are configured to conduct at least one real-time electronic negotiation querying session between the user and the at least one dedicated application server; where the at least one real-time electronic negotiation querying session is configured to: 1) receive, from the user, via the plurality of second programmable software objects, at least the following: a) at least one of: a plurality of personal event data parameters of at least one personal event and at least one demographic identifier, and b) a plurality of reference event data parameters of at least one reference event, where the plurality of reference event data parameters of the at least one reference event include a plurality time-related property data parameters for at least one time-related property of the at least one reference event; 2) allow, the user, via the plurality of second programmable software objects, to iteratively adjust the plurality of personal event data parameters of the at least one personal event and at least one of the at least one demographic identifier and the plurality of reference event data parameters of the at least one reference event so that, based on the anonymity level of the user, there is a matched subset of a minimal number of real individuals associated with the plurality of electronic data records of the at least one electronic source match the at least one personal event and the at least one reference event; 3) display, in real-time, an indication of how many real individuals are in the matched subset; 4) generate, with each adjustment iteration, a plurality of non-reversible synthetic electronic data records of a plurality of synthetic individuals, by utilizing at least one statistical technique to perform at least one of: self-recalculation of discrete values of the plurality of electronic data records of the matched subset and self-transformation categorical values of the plurality of electronic data records of the matched subset; and 5) electronically output, for the user, the plurality of non-reversible synthetic electronic data records of the plurality of synthetic individuals to at least one electronic destination associated with the user; and where the plurality of non-reversible synthetic electronic data records of the plurality of synthetic individuals: a) are statistically representative of the matched subset, b) have at least one synthetic identification identifier corresponding to at least one real identification identifier of a real individual from the matched subset, and c) cannot be utilized to identify any real individual from the matched subset.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A computer system, comprising:
a non-transitory memory storing instructions and
at least one processor;
wherein, when executing the instructions, the at least one processor is configured to:
receive at least one electronic query from a user, wherein the at least one electronic query comprises:
  a) at least one of:
    a plurality of personal event data parameters of at least one personal event and
    at least one demographic identifier, and b) a plurality of reference event data parameters of at least one reference event,
wherein the plurality of reference event data parameters of the at least one reference event comprise a plurality of time-related property data parameters for at least one time-related property of the at least one reference event;
assign an anonymity level to the user;
identify, in response to the at least one electronic query, a matched subset of matched data records for a number of real individuals from a plurality of electronic data records stored in at least one electronic source, based at least in part on:
 a) the anonymity level of the user,
 b) the at least one personal event, and
 c) the at least one reference event;
wherein the plurality of electronic data records comprises real identification identifiers of real individuals;
generate, based at least in part on the matched subset, a plurality of non-reversible synthetic electronic data records of a plurality of synthetic individuals by at least one of:
 self-recalculation of discrete values of the matched subset or
 self-transformation of categorical values of the matched subset;
analyze the matched subset and the plurality of non-reversible synthetic electronic data records of the plurality of synthetic individuals to generate at least one comparison report that is configured to confirm that the plurality of non-reversible synthetic electronic data records of the plurality of synthetic individuals is statistically representative of the matched subset;
wherein the plurality of non-reversible synthetic electronic data records of the plurality of synthetic individuals is unsuitable to be utilized to identify any real individual from the matched subset so as to protect privacy of the real individuals associated with the matched subset; and
wherein each respective synthetic identification identifier of the plurality of non-reversible synthetic electronic data records of the plurality of synthetic individuals corresponds to at least one real identification identifier of a real individual in the matched subset so as to avoid a generalization of the matched subset.

2. A computer-based method comprising:
receiving, by a computer processor, at least one electronic query from a user, wherein the at least one electronic query comprises:
 a) at least one of:
  a plurality of personal event data parameters of at least one personal event and
  at least one demographic identifier, and
 b) a plurality of reference event data parameters of at least one reference event,
wherein the plurality of reference event data parameters of the at least one reference event comprise a plurality of time-related property data parameters for at least one time-related property of the at least one reference event;
assigning, by the computer processor, an anonymity level to the user;
identifying, by the computer processor, in response to the at least one electronic query, a matched subset of matched data records for a number of real individuals from a plurality of electronic data records stored in at least one electronic source, based at least in part on:
 a) the anonymity level of the user,
 b) the at least one personal event, and
 c) the at least one reference event;
wherein the plurality of electronic data records comprises real identification identifiers of real individuals;
generating, by the computer processor, based at least in part on the matched subset, a plurality of non-reversible synthetic electronic data records of a plurality of synthetic individuals by at least one of:
 self-recalculation of discrete values of the matched subset or
 self-transformation of categorical values of the matched subset;
analyzing, by the computer processor, the matched subset and the plurality of non-reversible synthetic electronic data records of the plurality of synthetic individuals to generate at least one comparison report that is configured to confirm that the plurality of non-reversible synthetic electronic data records of the plurality of synthetic individuals is statistically representative of the matched subset;
wherein the plurality of non-reversible synthetic electronic data records of the plurality of synthetic individuals is unsuitable to be utilized to identify any real individual from the matched subset so as to protect privacy of the real individuals associated with the matched subset; and
wherein each respective synthetic identification identifier of the plurality of non-reversible synthetic electronic data records of the plurality of synthetic individuals corresponds to at least one real identification identifier of a real individual in the matched subset so as to avoid a generalization of the matched subset.

\* \* \* \* \*